(12) United States Patent
Obara et al.

(10) Patent No.: US 8,445,551 B2
(45) Date of Patent: May 21, 2013

(54) SOLID ELECTROLYTE MEMBRANE FOR FUEL CELL AND PROCESS FOR PRODUCING SAME

(75) Inventors: Yoshihiko Obara, Matsusaka (JP); Katsutoshi Suzuki, Hino (JP); Toru Tanaka, Fujimino (JP); Haruhiko Komoriya, Iruma-gun (JP)

(73) Assignee: Central Glass Company, Ltd., Ube-shi (JP)

( * ) Notice: Subject to any disclaimer, the term of this patent is extended or adjusted under 35 U.S.C. 154(b) by 0 days.

(21) Appl. No.: 13/389,808

(22) PCT Filed: Aug. 19, 2010

(86) PCT No.: PCT/JP2010/063957
§ 371 (c)(1),
(2), (4) Date: Feb. 10, 2012

(87) PCT Pub. No.: WO2011/021648
PCT Pub. Date: Feb. 24, 2011

(65) Prior Publication Data
US 2012/0142791 A1 Jun. 7, 2012

(30) Foreign Application Priority Data
Aug. 20, 2009 (JP) .................. 2009-191416

(51) Int. Cl.
*H01M 2/16* (2006.01)
*C08G 77/28* (2006.01)
*C07F 7/08* (2006.01)

(52) U.S. Cl.
USPC .................. 521/27; 556/428; 528/25; 528/27; 528/28; 528/30

(58) Field of Classification Search
None
See application file for complete search history.

(56) References Cited

U.S. PATENT DOCUMENTS

| | | | | |
|---|---|---|---|---|
| 3,012,006 A | * | 12/1961 | Holbrook et al. | 428/391 |
| 3,716,517 A | * | 2/1973 | Pittman et al. | 528/34 |
| 4,578,504 A | * | 3/1986 | Hammar | 560/112 |
| 5,162,155 A | * | 11/1992 | Berndt et al. | 428/405 |
| 5,283,310 A | * | 2/1994 | Armand et al. | 528/30 |
| 5,721,328 A | * | 2/1998 | Armand et al. | 526/243 |
| 6,414,139 B1 | * | 7/2002 | Unger et al. | 556/413 |
| 6,956,083 B2 | | 10/2005 | Kerr et al. | |
| 2002/0022734 A1 | * | 2/2002 | Marhold et al. | 556/415 |
| 2002/0061431 A1 | | 5/2002 | Koyama et al. | |
| 2004/0033407 A1 | | 2/2004 | Koyama et al. | |
| 2004/0116617 A1 | | 6/2004 | Ishihara et al. | |
| 2005/0179013 A1 | * | 8/2005 | Dalton et al. | 252/582 |
| 2005/0271922 A1 | | 12/2005 | Koyama et al. | |
| 2006/0041075 A1 | * | 2/2006 | Kerr et al. | 525/242 |
| 2006/0286424 A1 | | 12/2006 | Sugiyama | |
| 2006/0292417 A1 | | 12/2006 | Koyama et al. | |
| 2012/0100458 A1 | * | 4/2012 | Kishimoto et al. | 429/494 |

FOREIGN PATENT DOCUMENTS

| | | |
|---|---|---|
| JP | 2000-80166 A | 3/2000 |
| JP | 2002-110174 A | 4/2002 |
| JP | 2005-162623 A | 6/2005 |
| JP | 2008-74989 A | 4/2008 |
| WO | WO 02/072643 A1 | 9/2002 |

* cited by examiner

Primary Examiner — Robert S Loewe
(74) Attorney, Agent, or Firm — Crowell & Moring LLP

(57) ABSTRACT

Disclosed are a solid electrolyte membrane for fuel cells, which is characterized by that there has been used a silicone resin obtained by subjecting a methide series siloxane compound having a specific, strong acid bis(perfluoroalkanesulfonyl)methide moiety, a specific polysiloxane compound, and a specific silane compound to a cross-linking reaction, and its production process. This membrane has heat resistance, is superior in chemical stability, has a good proton conductivity even under a low water content condition, and has a low methanol permeability.

17 Claims, No Drawings

SOLID ELECTROLYTE MEMBRANE FOR FUEL CELL AND PROCESS FOR PRODUCING SAME

TECHNICAL FIELD

The present invention relates to a solid electrolyte membrane for fuel cells and a process for producing the same.

BACKGROUND OF THE INVENTION

Fuel cell is a power-generating device that is high in power generation efficiency, and byproduct thermal energy can also be used effectively. Since fuel cell generates electricity by a chemical reaction, it has a power generation efficiency that is higher than that of other power-generating systems, in which electricity is generated secondarily, such as combusting fuel to make steam to rotate a turbine. The product of fuel cell is theoretically water, and it does not combust fuel. Therefore, emission of carbon dioxide is small, and it does not emit nitrogen oxides and sulfur oxides, which cause air pollution. Thus, it attracts attention as a next-generation clean energy.

In particular, a polymer electrolyte fuel cell (hereinafter abbreviated to PEFC) using a polymer solid electrolyte membrane as an electrolyte has a high output density of electric energy to be produced and is capable of low-temperature drive, that is, generating electricity at low temperatures. Therefore, it is developed for use of an automotive power source or of a home cogeneration system using a fuel cell as a power source or heat source, etc.

It is explained that fuel cell generates electricity by an opposite reaction to electrolysis of water. That is, electrolysis of water is a reaction in which electric energy is changed into chemical energy to decompose water and obtain oxygen molecules and hydrogen molecules. In contrast, fuel cell conducts a reaction to change chemical energy into electric energy. That is, in fuel cell, a fuel (hydrogen, methanol, natural gas, etc.) introduced to a hydrogen fuel electrode releases an electron by catalyst to become a hydrogen ion (proton). Since a solid electrolyte membrane for fuel cells has a property that is not permeable to electrons, the electron goes to an external circuit through an electrode, thereby allowing an electric current to flow. The proton moves in an electrolyte membrane and reacts at an air electrode as the opposite electrode with oxygen supplied and the electron returned from the external circuit, thereby producing water.

In a fuel cell, a solid electrolyte membrane for fuel cells is an important member that influences electric power generation performance. A solid electrolyte membrane for fuel cells is required to have a low cost and a high durability. In recent years, operating temperature in the electric power generation has increased to 120° C. to 150° C. for the purpose of high efficiency by using waste heat, the catalyst poisoning reduction, etc. Furthermore, it is required to omit or simplify a humidifier for the purpose of lowering the cost of a fuel cell system, that is, to have a high proton conductivity even under a low humidified condition of 20% or less humidity.

For a solid electrolyte membrane for fuel cells, a perfluorocarbon sulfonic acid series polymer is used. As solid electrolytes for fuel cells by perfluorocarbon sulfonic acid series polymers, a trade name Nafion from US Aldrich Co., a trade name Flemion from Asahi Glass Co., Ltd., a trade name Aciplex from Asahi Kasei Corporation, a trade name GORE-SELECT from Japan Gore-Tex Inc., etc. are on the market.

Sulfonic acid group in a perfluorocarbon sulfonic acid series polymer shows hydrophilicity with water and makes a cluster moiety in the polymer. It is believed to show proton conductivity by the movement of protons with water molecules among clusters. Therefore, it is necessary to have a condition that water is contained in a solid electrolyte membrane for fuel cells in order to obtain a high proton conductivity.

Perfluorocarbon sulfonic acid series polymers are superior in chemical stability, but glass transition temperature is low, and heat resistance is low. Therefore, there has been a problem that operating temperature is low as being 70° C. to 100° C. Furthermore, there are problems that proton conductivity lowers upon a low humidification and that water cannot be maintained in the solid electrolyte membrane for fuel cells, at 100° C. or higher, thereby greatly lowering proton conductivity and mechanical characteristics.

Of PEFC's, a direct-methanol fuel cell (hereinafter abbreviated to DMFC) uses methanol in place of hydrogen and directly makes this react at an electrode to generate electricity. Unlike other fuel cells that hydrogen is converted to a hydrogen ion (proton) and an electron by removing the electron from the hydrogen by catalyst on an anode side (fuel electrode), in DMFC, methanol reacts directly with water by catalyst on the anode electrode and changes to proton, electron or carbon dioxide.

In the case of using methanol as a fuel, there occurs a crossover phenomenon that a part of methanol passes from the anode side to the cathode side, thereby causing a problem of lowering of the electric potential of the air electrode besides fuel loss.

Furthermore, a perfluorocarbon sulfonic acid series electrolyte membrane has many production steps. This tends to increase the cost. Therefore, research and development is conducted on a film prepared by introducing sulfonic acid group to an aromatic hydrocarbon series polymer, for reducing the cost.

For example, Patent Publication 1 discloses an electrolyte membrane prepared by introducing sulfonic acid group to polyarylene sulfide sulfone and/or polyarylene sulfone, but it deteriorates by the release of sulfonic acid group.

Furthermore, Patent Publication 2 discloses an aromatic hydrocarbon series electrolyte membrane prepared by introducing a sulfoalkyl group to a side chain in order to suppress the release of sulfonic acid from the aromatic ring, but it has a problem of inferiority in oxidation resistance. Thus, deterioration by oxidation is problematic in aromatic hydrocarbon series electrolyte membranes. In one prepared by directly introducing sulfonic acid group or the like to an aromatic, a noticeable release of sulfonic acid tends to occur at high temperatures. Therefore, it is not preferable as a high-temperature operating membrane. Furthermore, aromatic hydrocarbon series electrolyte membranes as a whole have a problem that proton conductivity lowers extremely upon a low humidification.

Furthermore, Patent Publication 3 mentions an electrolyte membrane prepared by a graft polymerization of a specific aromatic unit having a bistrifluoromethanesulfonylmethide group with no use of a sulfonic acid group. It is disclosed that an electrolyte membrane containing a perfluorosulfonyl group has proton conductivity even under a low water content condition. It is, however, necessary to conduct a graft polymerization to a styrene series polymer. This requires much effort for the production, causing a problem in terms of cost.

PRIOR ART PUBLICATIONS

Patent Publications

Patent Publication 1: Japanese Patent Application Publication 2000-80166.
Patent Publication 2: Japanese Patent Application Publication 2002-110174.
Patent Publication 3: Japanese Patent Application Publication 2005-162623.

SUMMARY OF THE INVENTION

In conventional solid electrolyte membranes for fuel cells, which use sulfonic acid group as an acid group, there has been a problem that the sulfonic acid group is released at high temperatures. Furthermore, in order to increase proton conductivity, it is under consideration to increase the amount of the sulfonic acid group introduced, but there has been a problem that the electrolyte membrane becomes weak as the amount of the sulfonic acid group introduced increases.

Furthermore, a solid electrolyte membrane for fuel cells is required to have a good proton conductivity even under a low humidified condition in addition to mechanical heat resistance and chemical stability, also to have a low methanol permeability for suppressing a crossover phenomenon of methanol, and also to have a low price. A solid electrolyte membrane for fuel cells, which satisfies all of these, is not known presently.

It is an object of the present invention to provide a solid electrolyte membrane for fuel cells, which is superior in heat resistance and chemical stability, has a good proton conductivity under a low humidified condition, and also has a low methanol permeability for suppressing a crossover phenomenon of methanol, and its raw material compound. Furthermore, it is an object to provide a process for producing the solid electrolyte membrane for fuel cells, which is industrially easy and appropriate for mass production.

The present inventors have succeeded in obtaining a specific methide series silane compound having a bis(perfluoroalkanesulfonyl)methide group, which is a strong acid ion-exchange group, and have obtained a silicone resin prepared by using the methide series compound as a condensation unit. We have found that the obtained silicone resin is preferably used as a solid electrolyte membrane for fuel cells.

The present invention is as follows.

[Invention 1]

A polysiloxane compound comprising the following condensation unit (a).

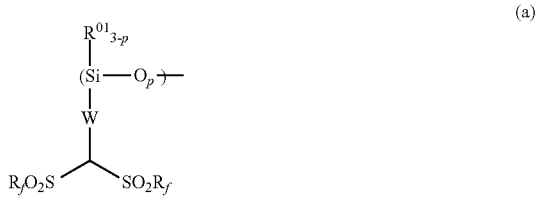

(In the formula, each of $R^{01}$ is independently a hydrogen atom, alkyl group, alkenyl group or aryl group and represents an organic group optionally having a cross-linking group, W represents a single bond or bivalent group, and $R_f$ represents a $C_{1-9}$ perfluoroalkyl group, and p represents 1, 2 or 3.) In case that p is 1, the number of siloxane bonds is one, and it becomes an end of the polysiloxane compound. In case that p is 2, it has two of the siloxane bonds. Furthermore, in case that p is 3, it has three of the siloxane bonds, and the polysiloxane compound turns to have a network structure.

[Invention 2]

A polysiloxane compound according to Invention 1, wherein W is a single bond, a $C_{1-10}$ straight-chain or branched-chain alkylene group, or a bivalent organic group represented by general formula (6).

(In the formula, m represents an integer of 2-5, n represents an integer of 0-5, and A represents any group represented by the following formula (7).)

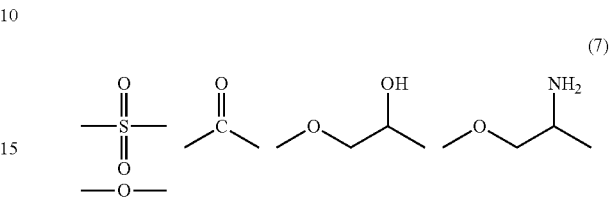

[Invention 3]

A polysiloxane compound according to claim 1 or claim 2, further comprising the following condensation unit (b).

(In the formula, each of $R^{02}$ is independently a hydrogen atom, alkyl group, alkenyl group or aryl group and represents an organic group optionally having a cross-linking group, and p represents 1, 2, 3 or 4.)

In case that q is 1, the number of siloxane bonds is one, and it becomes an end of the polysiloxane compound. In case that q is 2, the number of siloxane bonds is two. Furthermore, in case that q is 3 and 4, the numbers of siloxane bonds are three and four, and the polysiloxane compound turns to have a network structure.

[Invention 4]

A polysiloxane compound according to any of Invention 1 to Invention 3, wherein an end of the polysiloxane skeleton is capped with a group represented by the following formula (c).

(In the formula, each of $R^{03}$ independently represents a hydrogen atom, alkyl group, alkenyl group or aryl group.)

[Invention 5]

A polysiloxane compound according to any of Invention 1 to Invention 4, comprising 1-150 units of the condensation unit (a) and 0-150 units of the condensation unit (b).

[Invention 6]

A polysiloxane compound according to any of Invention 1 to Invention 5, which comprises as the cross-linking group at least one of at least one kind selected from the group consisting of hydroxy group, mercapto group, carboxyl group, amino group, epoxy group, alkenyl group, alkynyl group, acryloyl group, methacryloyl group, chlorosilyl group, alkoxysilyl group, and hydrosilyl group.

[Invention 7]

A polysiloxane composition comprising a cross-linking agent and the polysiloxane compound according to any of Invention 1 to Invention 6.

[Invention 8]

A polysiloxane composition according to Invention 7, further comprising a siloxane compound represented by the following formula (8).

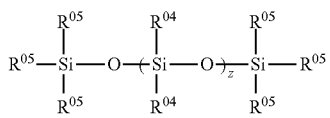
(8)

(In the formula, each of $R^{04}$ and $R^{05}$ independently represents a hydrogen atom, alkyl group, alkenyl group or aryl group, and at least two of $R^{04}$ and $R^{05}$ have cross-linking groups. z represents an integer of 0-150.)

[Invention 9]

A polysiloxane composition according to Invention 7 or Invention 8, wherein the cross-linking agent is at least one selected from the group consisting of isocyanate compounds, epoxy compounds, aldehyde series compounds, chlorosilanes, alkoxysilanes, melamine series compounds, sulfur or sulfur compounds, hydrosilane peroxides, and azo compounds.

[Invention 10]

A polysiloxane composition according to Invention 7 or Invention 8, wherein the cross-linking agent is a silane compound represented by the following formula (9).

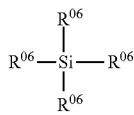
(9)

(In the formula, each of $R^{06}$ independently represents a hydrogen atom, a $C_{1-6}$ straight-chain or branched-chain alkyl group, a $C_{2-7}$ alkenyl group, or a $C_{6-8}$ aryl group, and at least three of $R^{06}$ are cross-linking groups or groups having a cross-linking group.)

[Invention 11]

A silicone resin obtained by subjecting the polysiloxane composition according to any one of Invention 7 to Invention 10 to a cross-linking reaction.

[Invention 12]

A solid electrolyte membrane comprising the silicone resin according to Invention 11.

[Invention 13]

A solid electrolyte membrane according to Invention 12, wherein the condensation unit (a) component amounts to 5 mass % or more of mass of the membrane.

[Invention 14]

A methide series silane compound represented by general formula (4).

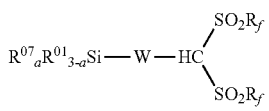
(4)

(In the formula, $R^{07}$ represents a fluorine atom, chlorine atom, bromine atom, iodine atom or alkoxy group, $R^{01}$ represents a hydrogen atom, alkyl group, alkenyl group or aryl group, Rf represents a $C_{1-9}$ perfluoroalkyl group, and a represents an integer of 0-3. W represents a single bond or bivalent organic group.)

[Invention 15]

A methide series silane compound according to Invention 14, wherein W is a single bond, a $C_{1-10}$ straight-chain or branched-chain alkylene group, or a bivalent organic group represented by general formula (6)

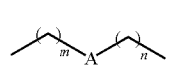
(6)

(In the formula, m represents an integer of 2-5, n represents an integer of 0-5, and A represents any group represented by the following formula (7).).

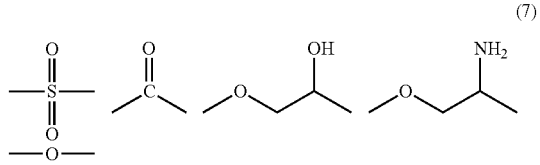
(7)

[Invention 16]

A methide series silane compound according to Invention 14 or Invention 15, wherein each of $R^{01}$ and $R^{07}$ is independently a $C_{1-6}$ alkoxy group, a $C_{1-6}$ straight-chain or branched-chain alkyl group, a $C_{2-6}$ alkenyl group, or a $C_{6-8}$ aryl group.

[Invention 17]

A methide series silane compound according to any of Invention 14 to Invention 16, wherein a is an integer of 1-3.

DETAILED DESCRIPTION

A solid electrolyte membrane for fuel cells of the present invention is superior in heat resistance and chemical stability and has a good proton conductivity under a low humidified condition. Therefore, it is useful as a solid electrolyte membrane for fuel cells, which is for polymer electrolyte fuel cells.

As compared with conventional perfluorocarbon sulfonic acid series electrolyte membranes, a silicone resin of the present invention makes it possible to introduce a bis(perfluoroalkanesulfonyl)methide group, which is a strong acid group, with a high concentration, and shows a good proton conductivity under a low humidified condition. Furthermore, in addition to being high in proton conductivity, it has radical resistance, is superior in chemical stability, is free from mechanical strength deterioration such as that the membrane becomes weak at high temperatures, and is superior in methanol permeability. Therefore, it is useful as a solid electrolyte membrane for fuel cells, etc.

Furthermore, a methide series silane compound having a bis(perfluoroalkanesulfonyl)methide group, of the present invention is a raw material suitable for producing a silicone resin having a bis(perfluoroalkanesulfonyl)methide group. By using this as the raw material, it is possible to provide a process for producing easily and in large amounts a solid electrolyte membrane for fuel cells, etc., in an industrial scale.

In the present specification, "a methide series polysiloxane compound having a bis(perfluoroalkanesulfonyl)methide group" may be referred to as "a methide series polysiloxane compound", "a methide series silane compound having a bis(perfluoroalkanesulfonyl)methide group" may be referred to as "a methide series silane compound", "a polysiloxane compound not having a bis(perfluoroalkanesulfonyl)methide group" may be referred to simply as "a polysiloxane compound", and "a silane compound not having a bis(perfluoroalkanesulfonyl)methide group" may be referred to simply as "a silane compound".

In the present specification, when alkyl group, alkenyl group, alkoxy group, and aryl group are mentioned, each of them may have a substituent, unless otherwise explained.

In the present specification, "a cross-linking group" refers to a group that forms a covalent bond through its chemical reaction with another intramolecular or extramolecular cross-linking group.

In the following, a mode for carrying out the present invention is explained in detail.

[A Methide Series Silane Compound Having a Bis(Perfluoroalkanesulfonyl)Methide Group]

In a methide series silane compound represented by general formula (4),

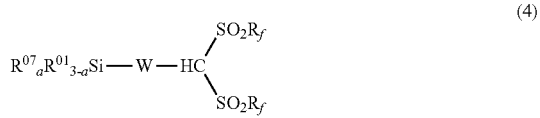

(4)

of the present invention, $R^{07}$ is a hydrolysable functional group or a group having a hydrolysable functional group and is a halogen atom (fluorine atom, chlorine atom, bromine atom or iodine. It is the same in the present specification.), an alkoxy group, or a group having a halogen atom or alkoxy group.

$R^{01}$ represents a hydrogen atom, alkyl group, alkenyl group or aryl group, may be a cross-linking group or a group having a cross-linking group, and has no hydrolysable group. Rf represents a $C_{1-9}$ perfluoroalkyl group, and a represents an integer of 0-3. W represents a single bond or a bivalent organic group.

In $R^{07}$ and $R^{01}$, a hydrogen atom or halogen atom, which is bonded to silicon, has a cross-linking property. In the present invention, when a silicon bond is broken to form a radical, it may take a cross-linked structure.

As the alkoxy group, a $C_{1-6}$ alkoxy group is preferable. It can be exemplified by methoxy group, ethoxy group, n-propyl group, i-propyl group, n-butoxy group, etc. Methoxy group or ethoxy group is more preferable.

It is preferable that the alkyl group is a $C_{1-6}$ alkyl group that is straight-chain or branched-chain. It is possible to mention methyl group, ethyl group, n-propyl group, isopropyl group, n-butyl group, etc. Methyl group or ethyl group is more preferable.

It is preferable that the alkenyl group is a $C_{2-6}$ alkenyl group that is straight-chain or branched-chain. It is possible to mention vinyl group, allyl group, isopropenyl group, 3-butenyl group, 4-pentenyl group, etc. Vinyl group or allyl group is more preferable.

As the cross-linking group, it is possible to mention hydrogen atom (H of SiH bond), halogen atom, hydroxy group, mercapto group, carboxyl group, amino group, epoxy group, alkenyl group, alkynyl group, acryloyl group, methacryloyl group, chlorosilyl group, alkoxysilyl group, or hydrosilyl group, etc. Hydrogen atom (H of SiH bond), alkenyl group, and vinyl group are preferable.

It suffices that the group having a cross-linking group is an organic group having the cross-linking group. This organic group is preferably an alkyl group. The alkyl group and the cross-linking group are optionally bonded to have a bivalent group therebetween. (Meth)acryloyloxy group, etc. are also preferable. Furthermore, the alkenyl group that is an alkyl group having a vinyl group at an end is preferable.

The aryl group is preferably a $C_{6-8}$ aryl group. It is possible to mention phenyl group, o-tolyl group, m-tolyl group, p-tolyl group, o-ethylphenyl group, m-ethylphenyl group, p-ethylphenyl group, 2,4-dimethylphenyl group, etc. Phenyl group is particularly preferable.

As Rf, it is possible to mention trifluoromethyl group, pentafluoroethyl group, heptafluoro-n-propyl group, heptafluoro-i-propyl group, nonafluorobutyl group, etc. Trifluoromethyl group or pentafluoroethyl group are preferable.

The integer "a" represents the number of hydrolysable groups or groups having a hydrolysable group, which are contained in one molecule. When "a" is 1-3, a methide series silane compound represented by general formula (4) is used in the condensation reaction.

It is preferable that W is a $C_{1-10}$ straight-chain or branched-chain alkylene group or a bivalent organic group represented by general formula (6).

(6)

m represents an integer of 2-5, and n represents an integer of 0-5. A represents any group represented by the following formula (7).

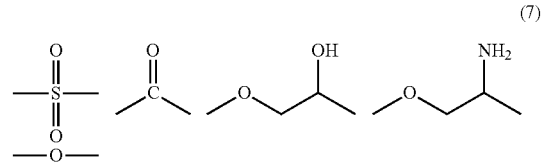

(7)

A process for synthesizing a methide silane compound having a bis(perfluoroalkanesulfonyl)methide group, which is represented by general formula (4), is explained in the following.

It is possible to synthesize bis(perfluoroalkanesulfonyl)methane and alkenyl bis(perfluoroalkanesulfonyl)methane, which are strong acid compounds having a bis(perfluoroalkanesulfonyl)methide group and become raw materials, by publicly known methods (e.g., Journal of Organic Chemistry, Vol. 38, No. 19, 1973, 3358, etc.). For example, they are synthesized by the following reactions (Grignard reactions).

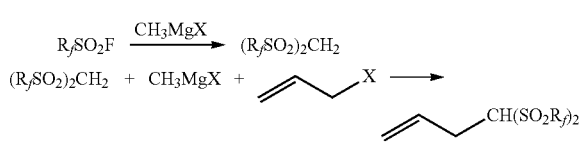

In these formulas, X represents a halogen atom, and chlorine atom, bromine atom and iodine atom are preferable. $R_f$ represents a $C_{1-9}$ perfluoroalkyl group in general formula (4).

It is possible to synthesize a methide series silane compound by making a hydrosilane to act on the alkenyl bis (perfluoroalkanesulfonyl)methane. Hydrosilylation reaction of a group (allyl group, etc.) having a carbon-carbon unsaturated bond, such as alkenyl group, proceeds by a publicly known method. With this, it is possible to synthesize a methide series silane compound containing a bis(perfluoroalkanesulfonyl)methide group. It is synthesized, for example, by the following reaction.

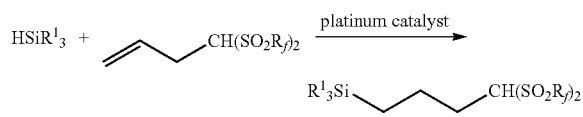

$R^1$ and $R_f$ are defined as in general formula (4).

Furthermore, there proceed by publicly-known methods the following reactions of a bis(perfluoroalkanesulfonyl) methane with, for example, sulfonyl halide, carboxylic acid halide, and epoxide. Thus, it is possible to synthesize methide series silane compounds having a bis(perfluoroalkanesulfonyl)methide group.

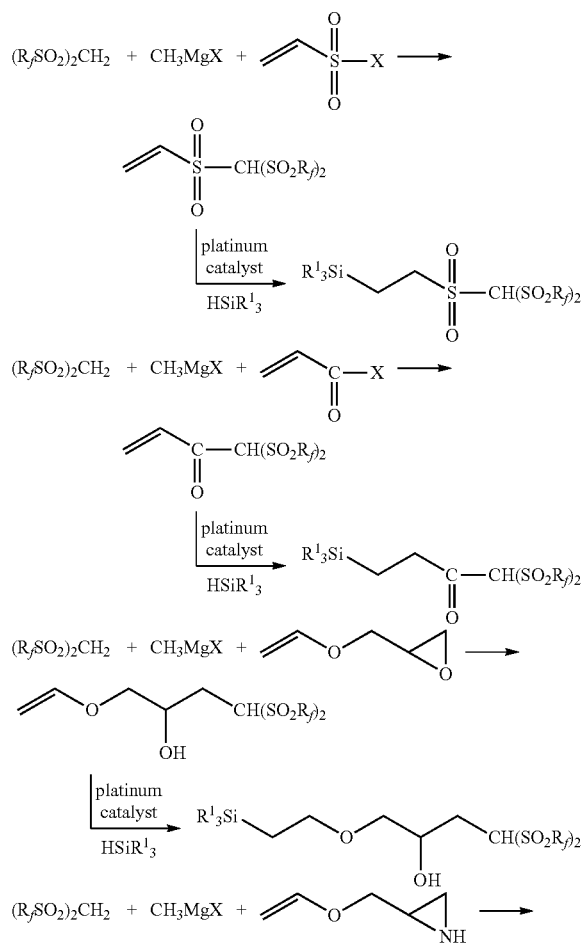

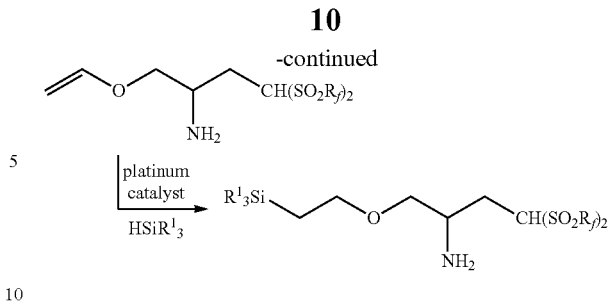

X represents a halogen atom, $R^1$ shows the same meaning as that of $R^{01}$ of general formula (4), and $R_f$ is defined as in general formula (4).

As a reaction catalyst (In the reaction formulas, it is expressed as platinum catalyst) of these reactions, one for accelerating a hydrosilylation addition reaction between alkenyl group and SiH group is used. For example, it is possible to mention platinum group metals or compounds of these, such as platinum, palladium, rhodium, etc., chloroplatinic acid, alcohol-modified chloroplatinic acid, coordination compounds between chloroplatinic acid and olefins, vinyl siloxane or acetylenic compounds, tetrakis(triphenylphosphine)palladium, platinum divinylsiloxane, platinum cyclic vinylmethylsiloxane, tris(dibenzylidene acetone)diplatinum, bis(ethylene)tetrachlorodiplatinum, cyclooctadiene dichloroplatinum, bis(cyclooctadiene)platinum, bis(dimethylphenylphosphine)dichloroplatinum, platinum carbon, chlorotris (triphenylphosphine)rhodium, etc. The reaction catalyst in the present reaction is preferably a platinum compound, and particularly dichloro(1,5-cyclooctadiene)platinum(II) is preferable.

Furthermore, the amount of mixing of the reaction catalyst is 0.5 ppm or more and 1000 ppm or less, when expressed by the mass ratio of the metal element in the catalyst to mass of the alkenyl group-containing compound. If it is less than 0.5 ppm, the advantageous effect of the reaction catalyst is small. Even if it is added by more than 1000 ppm, the advantageous effect does not change. Therefore, it is uneconomical. In view of an effective range of the reaction catalyst, it is preferable to be particularly in a range of 1 ppm to 500 ppm. More preferably, it is a range of 10 ppm to 100 ppm.

The amount of mixing of the hydrosilane compound is 1 equivalent to 5 equivalents relative to the alkenyl group-containing compound. If it is less than 1 equivalent, the alkenyl group-containing compound becomes excessive. With this, the reaction is not completed, and yield is lowered. Therefore, it is not preferable. Even if it is added by more than 5 equivalents, there is no improvement in conversion of the alkenyl group-containing compound. Therefore, it is not preferable. More preferably, it is from one equivalent to three equivalents.

Examples of a methide series silane compound represented by general formula (4), which is obtained by the above-mentioned reaction, are nonlimitatively listed in the following. In a methide series silane compound represented by general formula (4), W represents a short bond, a $C_{1-10}$ straight-chain or molecule-chain alkylene group, or a bivalent organic group and optionally has a sulfonyl group, carbonyl group, ether group, hydroxy group, or amino group.

W is indicative of, for example, $-CH_2-$, $-CH_2-CH_2-$, $-CH_2-CH_2-CH_2-$, $-CH_2-CH(CH_3)-$, $-CH_2-CH_2-CH_2-CH_2-$, $-CH_2-SO_2-$, $-CH_2-CH_2-SO_2-$, $-CH_2-CH_2-CH_2-SO_2-$, $-CH_2-CH(CH_3)-SO_2-$, $-CH_2-CH_2-CH_2-CH_2-SO_2-$, $-CH_2-CO-$, $-CH_2-CH_2-CO-$, $-CH_2-CH_2-CH_2-CO-$, $-CH_2-CH(CH_3)-CO-$, $-CH_2-CH_2-$ $CH_2$—$CH_2$—CO—, —$CH_2$—O—$CH_2$—CH(OH)—$CH_2$—, —$CH_2$—$CH_2$—O—$CH_2$—CH(OH)—$CH_2$—, —$CH_2$—$CH_2$—$CH_2$—O—$CH_2$—CH(OH)—$CH_2$—, —$CH_2$—CH($CH_3$)—O—$CH_2$—CH(OH)—$CH_2$—, —$CH_2$—$CH_2$—$CH_2$—$CH_2$—O—$CH_2$—CH(OH)—$CH_2$—, —$CH_2$—O—$CH_2$—CH($NH_2$)—$CH_2$—, —$CH_2$—$CH_2$—O—$CH_2$—CH($NH_2$)—$CH_2$—, —$CH_2$—$CH_2$—$CH_2$—O—$CH_2$—CH($NH_2$)—$CH_2$—, —$CH_2$—CH($CH_3$)—O—$CH_2$—CH($NH_2$)—$CH_2$—, —$CH_2$—$CH_2$—$CH_2$—$CH_2$—O—$CH_2$—CH($NH_2$)—$CH_2$—, —$CH_2$—O—$CH_2$—$CH_2$—, —$CH_2$—$CH_2$—O—$CH_2$—$CH_2$—, —$CH_2$—$CH_2$—$CH_2$—O—$CH_2$—$CH_2$—, —$CH_2$—CH($CH_3$)—O—$CH_2$—$CH_2$—, or —$CH_2$—$CH_2$—$CH_2$—$CH_2$—O—$CH_2$—$CH_2$—. Preferably, they are —$CH_2$—$CH_2$—$CH_2$—, —$CH_2$—$CH_2$—$CH_2$—$CH_2$—, —$CH_2$—$CH_2$—$SO_2$—, —$CH_2$—$CH_2$—CO—, —$CH_2$—$CH_2$—O—$CH_2$—CH(OH)—$CH_2$—, —$CH_2$—$CH_2$—O—$CH_2$—CH($NH_2$)—$CH_2$—, and —$CH_2$—$CH_2$—O—$CH_2$—$CH_2$—.

Firstly, the methide series silane compound, in which W is formed of a $C_3$ straight-chain alkylene group, is listed.

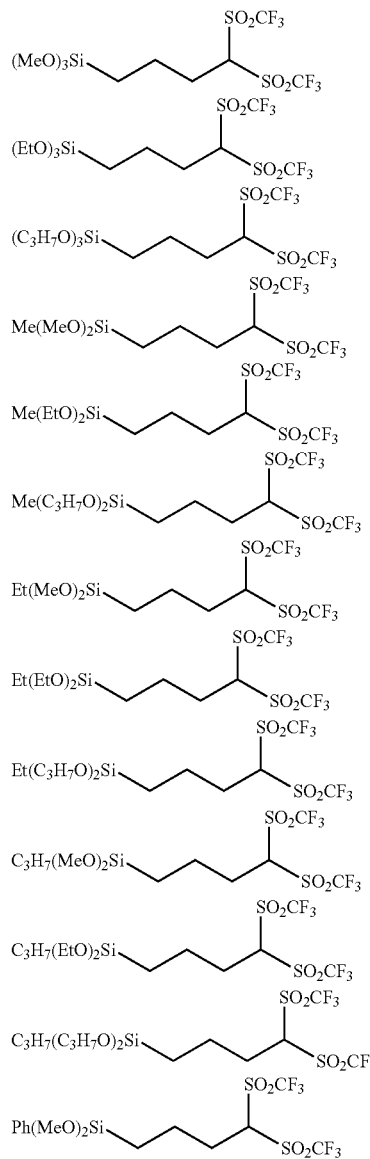

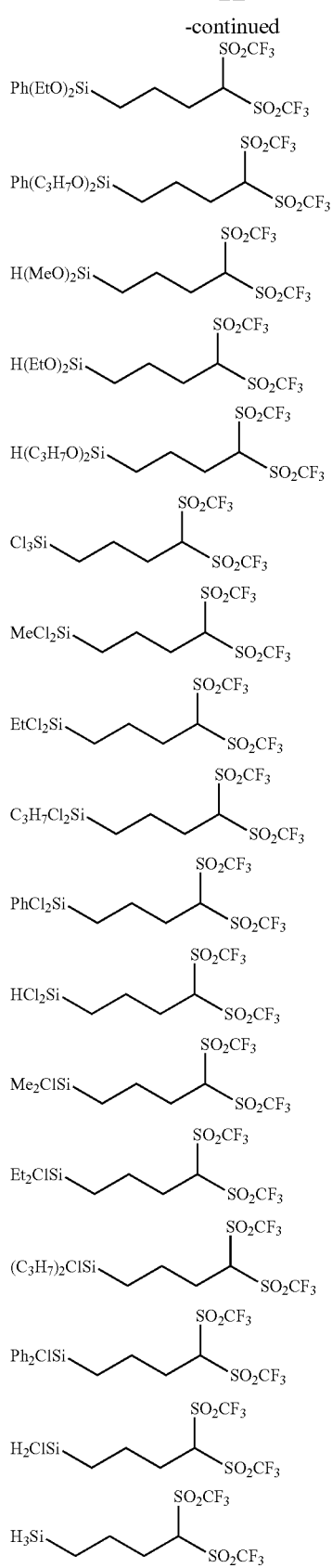

Then, the methide series silane compound, in which W is formed of a $C_4$ straight-chain alkylene group, is listed.

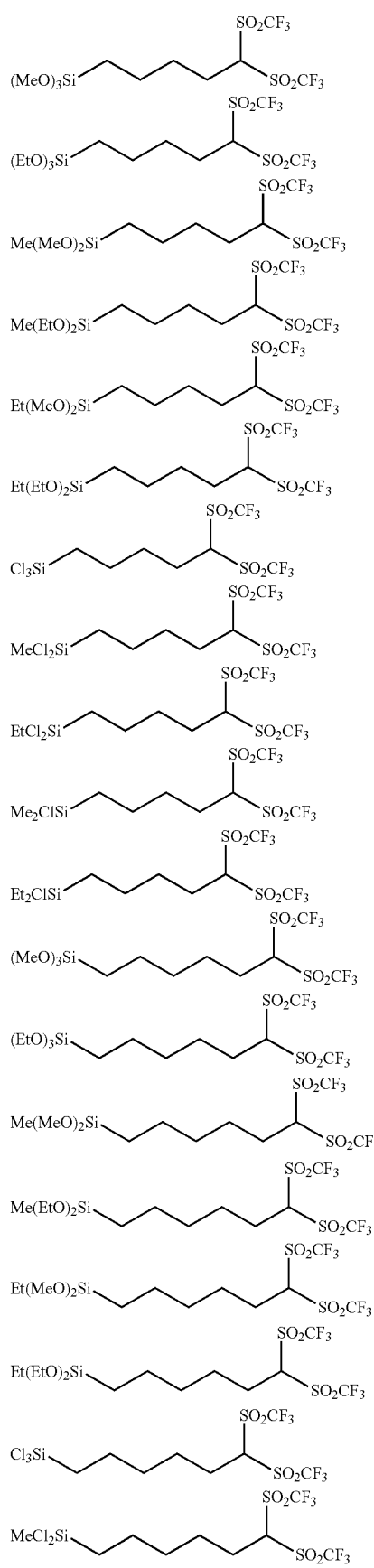
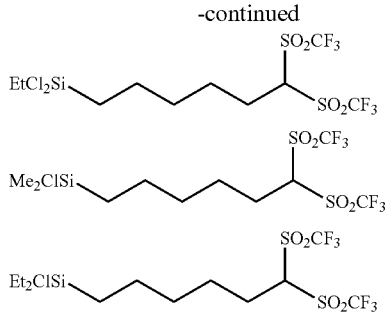
Then, the methide series silane compound, in which W is formed of a $C_2$ straight-chain alkylene group, is listed.
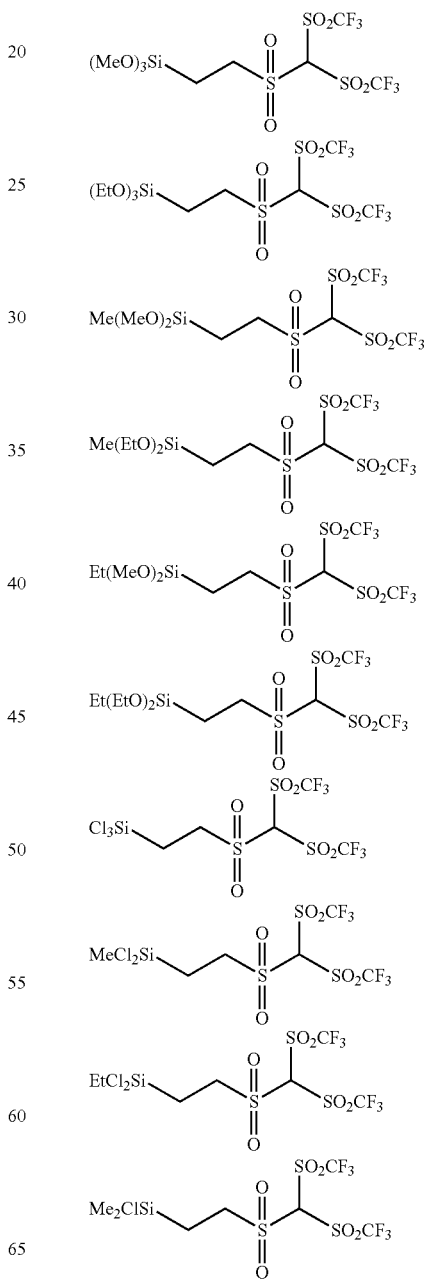

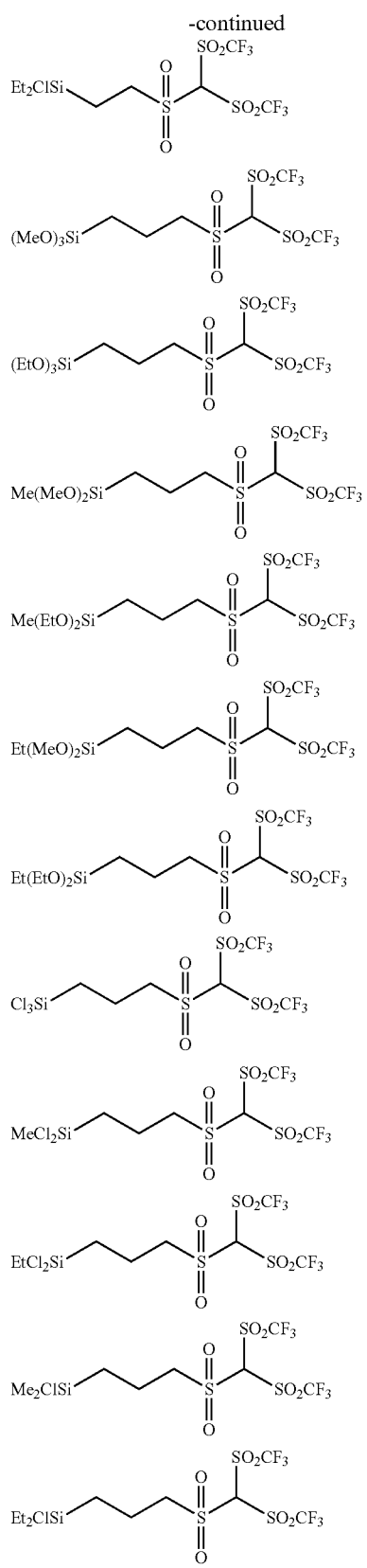
Then, the methide series silane compound, in which W is formed of a $C_2$ straight-chain alkylene group and a carbonyl group, is listed.
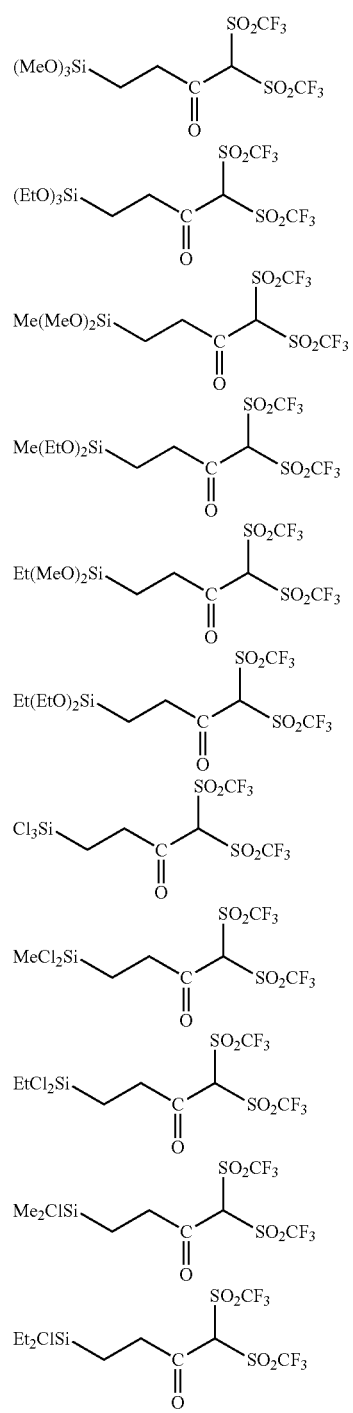
Then, the methide series silane compound, in which W has an ether group and a hydroxy group, is listed.
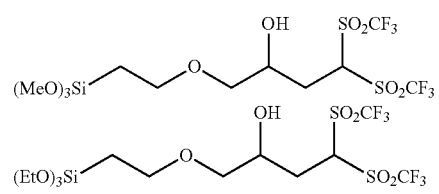

-continued

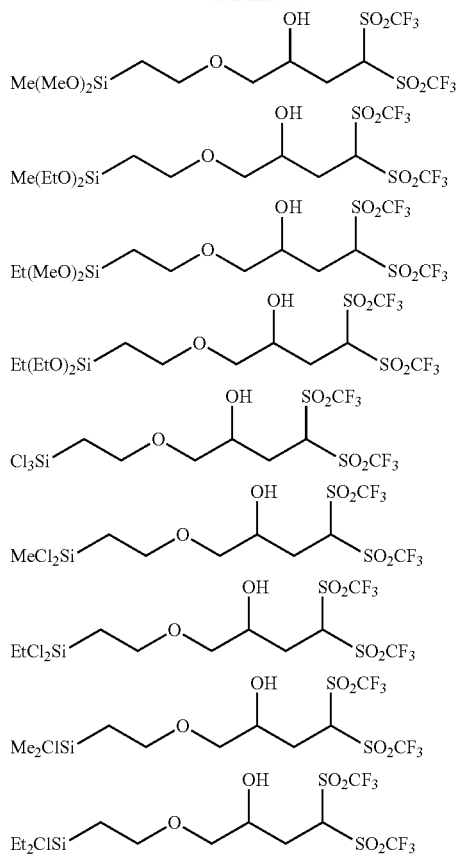

Then, the methide series silane compound, in which W has an ether group and an amino group, is listed.

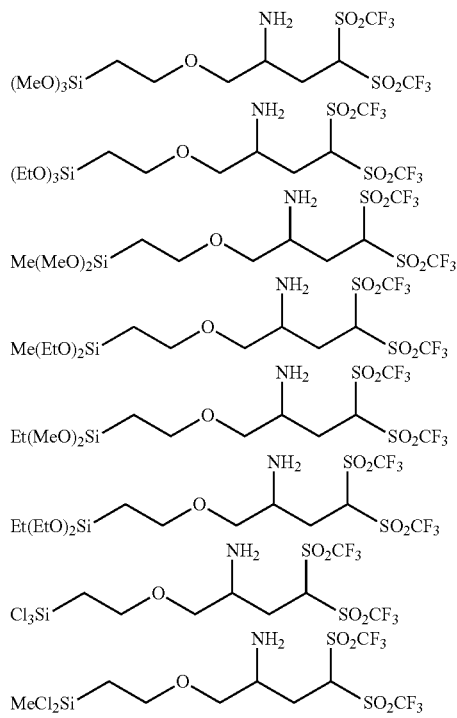

-continued

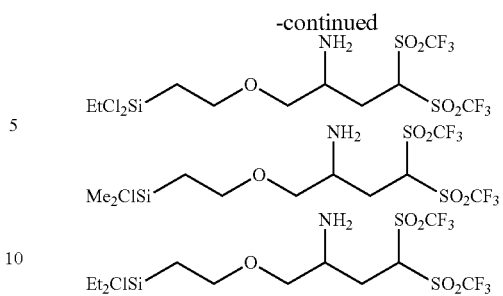

Then, the methide series silane compound, in which W has an ether group, is listed.

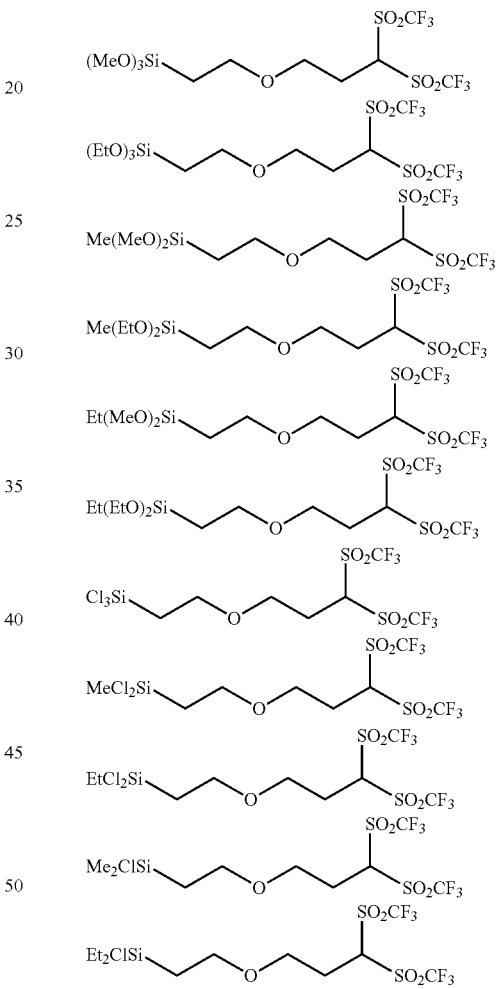

In the above-mentioned methide series silane compounds, Me represents a methyl group, and Et represents an ethyl group. Furthermore, the alkylene group may be branched, and it is naturally possible to replace $CF_3$ with $C_2F_5$ or $C_3F_7$.

[A Methide Series Polysiloxane Compound Having a Bis(Perfluoroalkanesulfonyl)Methide Group]

A methide series polysiloxane compound of the present invention is a polysiloxane compound having the following condensation unit (a). The polysiloxane compound is preferably a polysiloxane compound having at least one cross-linking group for a further polymerization or condensation with another compound.

The condensation unit (a) is a structure obtained by hydrolyzing a methide series silane compound represented by general formula (4). There occurs no change in the structure except the hydrolysable group, and structure of the methide series silane compound of the raw material is maintained.

A methide series polysiloxane compound of the present invention is a polysiloxane compound containing the following condensation unit (a).

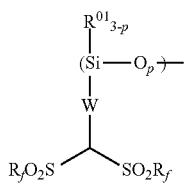
(a)

In the formula, $R^{01}$, W and Rf are respectively defined as in general formula (4). "3-p" is the number of $R^{01}$ bonded to Si, and p indicates the number of Si—O bonds and represents 1, 2 or 3. In the preparation of the solid electrolyte membrane, p can be an arbitrary value from 1, 2 and 3. It is preferable that the condensation unit (a) is not positioned at an end in the polysiloxane compound. It is preferable that p is mainly 2 or 3, particularly preferably 2.

Herein, when p is 3, 2 or 1, the bis(perfluoroalkanesulfonyl)methide moiety is represented by the following formula (1), (2) or (3), respectively.

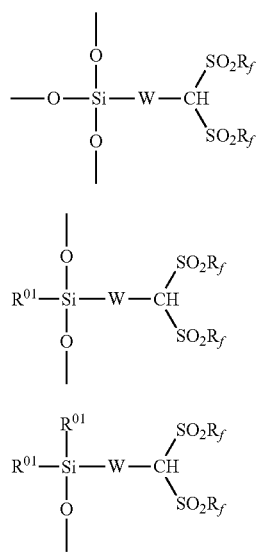
(1)
(2)
(3)

In the formula, $R^{01}$, W and Rf are defined as in general formula (4). As the bis(perfluoroalkanesulfonyl)bismethide moiety, specifically, it is possible to mention bis(perfluoroalkanesulfonyl)methide group, such as bis(trifluoromethanesulfonyl)methide group, bis(pentafluoroethanesulfonyl)methide group, (pentafluoroethanesulfonyl)(trifluoromethanesulfonyl)methide group, (trifluoromethanesulfonyl)(heptafluoropropanesulfonyl)methide group, and (nonafluorobutanesulfonyl)(trifluoromethanesulfonyl)imide group, etc. These condensation units represented by general formulas (1), (2) and (3) may be used at arbitrary proportions in the polysiloxane compound.

It is possible to make a condensation through hydrolysis between a methide series silane compound represented by general formula (4) and a silane compound having a hydrolysable group represented by general formula (10)

(10)

(In the formula, $R^{08}$ is a hydrolysable functional group or a group having a hydrolysable functional group, and it suffices to be a halogen atom (a fluorine atom, chlorine atom, bromine atom or iodine) or alkoxy group, or groups having these as substituents. $R^{02}$ represents a hydrogen atom, alkyl group, alkenyl group or aryl group, may be a cross-linking group or a group having a cross-linking group, and does not have a hydrolysable group. b represents an integer of 1-4.). With this, it is possible to obtain a polysiloxane compound containing the condensation unit (a) and the following condensation unit (b).

(b)

There occurs no change in the groups except the hydrolysable group in the hydrolysis reaction and the condensation reaction. Therefore, in the formula, $R^{02}$ is the same as $R^{07}$ in general formula (4), and q has the same meaning as that of p and represents 1, 2, 3 or 4. In the preparation of the solid electrolyte membrane, q can take an arbitrary value from 1, 2, 3 and 4. It is, however, preferable that the condensation (b) is not positioned at an end in the polysiloxane compound. It is preferable that p is mainly 2, 3 or 4, and particularly 2 is preferable.

In the silane compound having a hydrolysable group, which is represented by general formula (10), the explanations of $R^{07}$ and $R^{01}$ in general formula (4) correspond to those of $R^{08}$ and $R^{02}$, respectively.

A copolymerization of the following structural formula (c) by a hydrolysis of the silane compound, in which b is 1 in general formula (10), is useful for capping an end of the polysiloxane compound to be generated, thereby increasing stability.

(c)

In the hydrolysis reaction and the condensation reaction, there occurs no change in the groups other than the hydrolysable group. Therefore, in the formula, $R^{03}$ corresponds to $R^{02}$ in general formula (10), and the meaning of the symbol is the same as that of $R^{02}$.

In the polysiloxane compound, the degree of polymerization of a unit derived from the condensation unit (a) is 1-150, preferably 1-100, more preferably 1-50. The degree of polymerization of a unit derived from the condensation unit (b) is 0-150, preferably 0-100, more preferably 0-50. The number of the structural unit (c)'s corresponds to that of the ends of these condensation unit (a) and condensation unit (c).

A polysiloxane compound (a methide series polysiloxane compound) having a bis(perfluoroalkanesulfonyl)methide group of the present invention is made up of the condensation unit (a), the condensation unit (b), and according to need the structural unit (c) and can be represented by the following general formula (5).

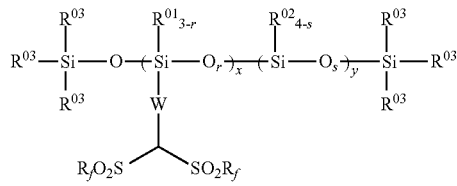

(5)

In the formula, each of $R^{01}$, $R^{02}$ and $R^{03}$ independently represents a hydrogen atom, alkyl group, alkenyl group, aryl group, or hydroxy group. At least two of $R^{01}$, $R^{02}$ and $R^{03}$ are cross-linking groups or groups in which a cross-linking group has been substituted. $R_f$ represents a $C_{1-9}$ perfluoroalkyl group, x and y represent degrees of polymerization, x represents an integer of 1-150, and y represents an integer of 0-150. x is preferably an integer of 1-100, more preferably an integer of 1-50. y is preferably an integer of 0-100, more preferably an integer of 0-50.

Furthermore, "3-r" represents the number of $R^{01}$'s bonded to Si, r represents the number of Si—O bonds in the parenthesis with x, "4-s" represents the number of $R^{02}$'s bonded to Si, and s represents the number of Si—O bonds in the parenthesis with y. Each of r and s independently an integer, r represents 1, 2 or 3, and s represents 1, 2, 3 or 4. It is preferable that r is 2 or 3, and particularly preferably 2. It is preferable that r and s are 2 at the same time. In the compound, r and s may be different for each Si molecule.

The explanations of $R^{01}$, $R^{02}$ and $R^{03}$ with respect to the condensation unit (a), the condensation unit (b) or the structural unit (c) correspond to $R^{01}$, $R^{02}$ and $R^{03}$, respectively. $R^{01}$, $R^{02}$ and $R^{03}$ except the cross-linking groups are preferably methyl group or phenyl group. It is particularly preferable that a polysiloxane compound represented by general formula (5) has a structure in which the molecular chain end is capped with a dimethylvinylsilyl group.

A methide series polysiloxane compound represented by general formula (5) has two or more cross-linking groups in one molecule. It is preferable that the cross-linking groups are contained to have a content of 0.01 mmol to 10.0 mmol per 1 g of mass of the polysiloxane compound. If the content of the cross-linking groups is less than 0.01 mmol, cure by cross-linking becomes insufficient. If it is contained by more than 10.0 mmol, the obtained silicone resin is high in hardness. This may cause difficulty in handling. Therefore, it is not preferable.

Furthermore, general formula (5) representing the methide series polysiloxane compound is not limited to a block copolymer or graft copolymer formed of the condensation unit (a) and the condensation unit (b), but may be a random copolymer or alternating copolymer. Therefore, x and y in the formula represent the number of respective condensation units in the molecule, and do not represent a block or graft structure. Due to ease of polymerization, a random polymer is preferable.

In the following, a polymerization reaction of the polysiloxane compound in the present invention is shown. Firstly, there is shown a reaction scheme (I) in an intermediate stage of a chain reaction, when polymerizing the polysiloxane compound using the silane compound having a hydrolysable group and a polymerizable group.

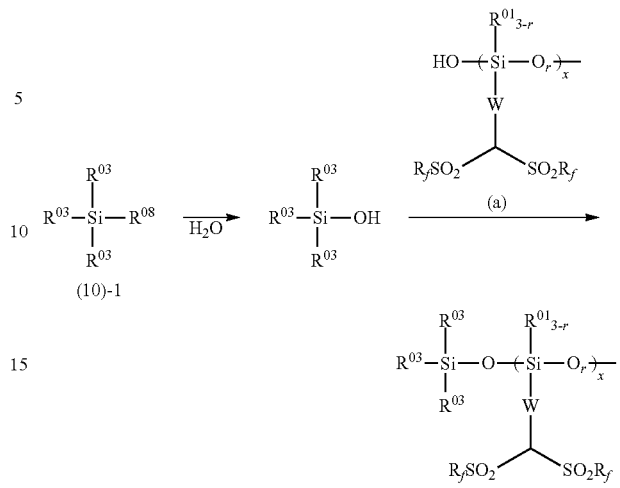

One of $R^{08}$ of general formula (10)-1, which is one example of general formula (10), which is the starting compound, is hydrolyzed to become an OH group, followed by a dehydration-condensation with the polysiloxane compound (a). In the formula, each of $R^{03}$ independently represents a hydrogen atom, alkyl group, alkenyl group, aryl group, or hydroxy group. $R_f$ represents a $C_{1-9}$ perfluoroalkyl group, x and y represent degrees of polymerization, and x represents an integer of 1-150.

As a typical one, there is shown a reaction scheme in an intermediate stage in a chain reaction using chlorodimethylvinylsilane as the starting compound.

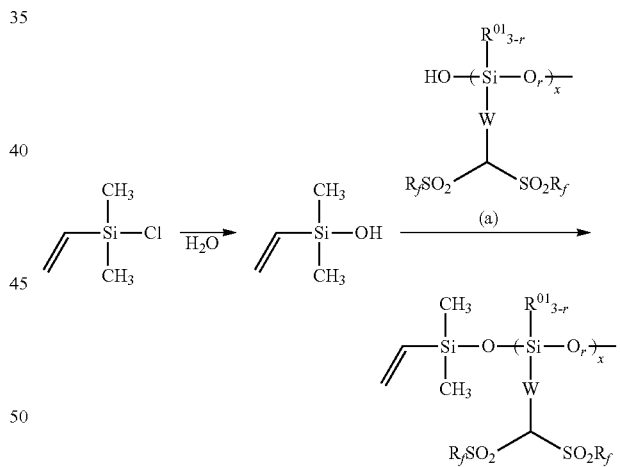

Cl group of the chlorodimethylvinylsilane, which is the starting compound, is hydrolyzed to become an OH group, followed by a dehydration-condensation with the polysiloxane compound (a).

The silane compound having a hydrolysable group and a polymerizable group, which is represented by general formula (10)-1, is nonlimitatively exemplified in the following. In the present invention, however, among these polymerizable silane compounds, chlorodimethylvinylsilane is preferably used, due to its availability and good reactivity.

As a silane compound (a polymerizable silane compound) having an alkenyl group as a cross-linking group, it is possible to mention silane compounds having (meth)acryloxy group, such as 3-(trimethoxysilyl)propyl methacrylate and 3-(trimethoxysilyl)propyl acrylate, allyl(chloromethyl)dimethylsilane, allylchlorodimethylsilane, allyltrichlorosilane, allyltriethoxysilane, allyltrimethoxysilane, allyltris(trimethylsilyloxy)silane, chlorodimethylvinylsilane, dichloromethylvinylsilane, diethoxymethylvinylsilane, dimethylethoxyvinylsilane, 1,3-divinyltetramethyldisiloxane, trichlorovinylsilane, dimethylethoxyvinylsilane, triethoxyvinylsilane, vinyltrimethoxysilane, or vinyltris(2-methoxyethoxy)silane.

Then, there is shown a reaction scheme (II) in an intermediate stage of a chain reaction, when polymerizing the polysiloxane compound using the silane compound having a hydrolysable group and no polymerizable group.

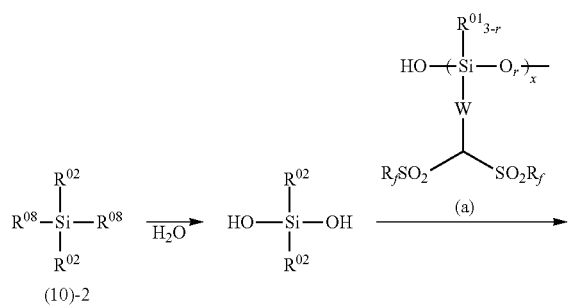

(10)-2

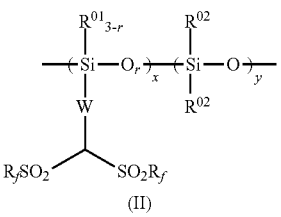

(II)

$R^{08}$ of general formula (10)-2, which is one example of general formula (10), which is the starting compound, is hydrolyzed to become an OH group, followed by a dehydration-condensation with the polysiloxane compound (a). In the formula, each of $R^{02}$ independently represents a hydrogen atom, alkyl group, alkenyl group, or aryl group. Rf represents a $C_{1-9}$ perfluoroalkyl group, x and y represent degrees of polymerization, x represents an integer of 1-150, and y represents an integer of 0-150.

As a typical one, there is shown a reaction scheme in an intermediate stage in a chain reaction using dichlorodimethylsilane as the starting compound.

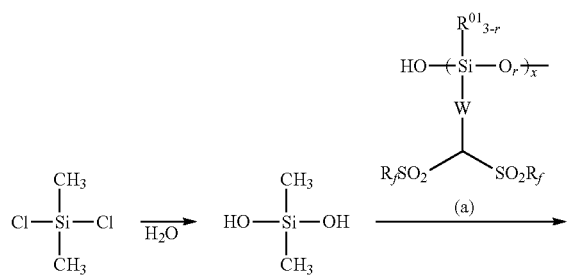

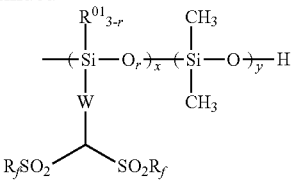

Cl group of the chlorodimethyl, which is the starting compound, is hydrolyzed to become an OH group, followed by a dehydration-condensation with the polysiloxane compound (a).

The silane compound having a hydrolysable group and no polymerizable group, which is represented by general formula (10)-2, is nonlimitatively exemplified in the following. In the present invention, however, among these polymerizable silane compounds, chlorodimethylvinylsilane is preferably used, due to its availability and good reactivity.

As the hydrolysable silane compound having no polymerizable group, it is possible to mention tetrachlorosilane, tetramethoxysilane, tetraethoxysilane, tetrapropylsilane, methoxytrimethylsilane, ethoxytriethylsilane, (chloromethyl) dimethylisopropoxysilane, [bicyclo[2.2.1]hept-5-en-2-yl] triethoxysilane, trimethyl[3-(triethoxysilyl)propyl] ammonium chloride, trimethoxy[3-(phenylamino)propyl] silane, trimethoxysilane, trimethoxyphenylsilane, trimethoxy(propyl)silane, trimethoxy(p-tolyl)silane, trimethoxy(methyl)silane, triethoxysilane, triethoxyphenylsilane, triethoxymethylsilane, triethoxyfluorosilane, triethoxyethylsilane, triethoxy-1H,1H,2H,2H-tridecafluoro-n-octylsilane, pentyltriethoxysilane, octadecyltrimethoxysilane, octadecyltriethoxysilane, N-[2-(N-vinylbenzylamino)ethyl]-3-aminopropyltrimethoxysilane hydrochloride, n-octyltriethoxysilane, n-dodecyltriethoxysilane, hexyltrimethoxysilane, hexyltriethoxysilane, ethyltrimethoxysilane, dodecyltrimethoxysilane, cyclohexyltrimethoxysilane, bis[3-(trimethoxysilyl)propyl]amine, benzyltriethoxysilane, 3-ureidopropyltriethoxysilane, 3-trimethoxysilylpropyl chloride, 3-glycidyloxypropyltrimethoxysilane, 3-chloropropyltriethoxysilane, 3-aminopropyltrimethoxysilane, 3-aminopropyltriethoxysilane, 3-(triethoxysilyl)propyl isocyanate, 3-(2-aminoethylamino) propyltrimethoxysilane, 3-(2-aminoethylamino)propyltriethoxysilane, 2-cyanoethyltriethoxysilane, 2-(3,4-epoxycyclohexyl)ethyltrimethoxysilane, 1-[3-(trimethoxysilyl) propyl]urea, 1,2-bis(trimethoxysilyl)ethane, (chloromethyl) triethoxysilane, (3-mercaptopropyl)trimethoxysilane, (3-mercaptopropyl)triethoxysilane, (3-bromopropyl)trimethoxysilane, tetrapropyl ortho-silicate, tetramethyl ortho-silicate, tetrakis(1,1,1,3,3,3-hexafluoroisopropyl)ortho-silicate, tetraisopropyl ortho-silicate, tetraethyl ortho-silicate, tetrabutyl ortho-silicate, dimethoxymethylphenylsilane, dimethoxydiphenylsilane, dimethoxydimethylsilane, dimethoxydi-p-tolylsilane, dimethoxy(methyl)silane, diethoxymethylsilane, diethoxydiphenylsilane, diethoxydimethylsilane, diethoxy(methyl)phenylsilane, diethoxy(3-glycidyloxypropyl)methylsilane, cyclohexyl(dimethoxy) methylsilane, 3-mercarptopropyl(dimethoxy)methylsilane, 3-glycidyloxypropyl(dimethoxy)methylsilane, 3-chloropropyldimethoxymethylsilane, 3-aminopropyldiethoxymethylsilane, 3-(2-aminoethylamino)propyldimethoxymethylsilane, 1,5-dichloro-1,1,3,3,5,5-hexamethyltrisiloxane, 1,3-dimethoxy-1,1,3,3-tetraphenyldisiloxane, 1,3-dichloro-1,1,3,3-tetramethyldisiloxane, 1,3-dichloro-1,1,3,3-tetraisopropyldisiloxane, 1,1,3,3,5,5,5-heptamethyl-3-(3- glycidyloxypropyl)trisiloxane, 3-chloropropyldichloromethylsilane, chloromethyl(dichloro)methylsilane, di-tert-butyldichlorosilane, dibutyldichlorosilane, dichloro(methyl)octadecylsilane, dichloro(methyl)phenylsilane, dichlorocyclohexylmethylsilane, dichlorodecylmethylsilane, dichlorodiethylsilane, dichlorodihexylsilane, dichlorodiisopropylsilane, dichlorodimethylsilane, dichlorodipentylsilane, dichlorodiphenylsilane, dichlorododecylmethylsilane, dichloroethylsilane, dichlorohexylmethylsilane, dichloromethylsilane, n-octylmethyldichlorosilane, tetrachlorosilane, 1,2-bis(trichlorosilyl)ethane, 3-chloropropyltrichlorosilane, bis(trichlorosilyl)acetylene, butyltrichlorosilane, cyclohexyltrichlorosilane, decyltrichlorosilane, dodecyltrichlorosilane, ethyltrichlorosilane, hexachlorodisilane, 1,1,2,2-tetrachloro-1,2-dimethyldisilane, isobutyltrichlorosilane, n-octyltrichlorosilane, phenyltrichlorosilane, thexyltrichlorosilane, trichloro(methyl)silane, trichloro(propyl)silane, trichloro-2-cyanoethylsilane, trichlorohexylsilane, trichlorooctadecylsilane, trichlorosilane, trichlorotetradecylsilane, (3-cyanopropyl)dimethylchlorosilane, (bromomethyl)chlorodimethylsilane, (chloromethyl)dimethylchlorosilane, 1,2-dichlorotetramethyldisilane, 1,3-dichloro-1,1,3,3-tetramethyldisiloxane, 1,5-dichloro-1,1,3,3,5,5-hexamethyltrisiloxane, α-(chlorodimethylsilyl)cumene, benzylchlorodimethylsilane, butylchlorodimethylsilane, chloro(decyl)dimethylsilane, chloro(dodecyl)dimethylsilane, chlorodiisopropylsilane, chlorodimethylphenylsilane, chlorodimethylpropylsilane, chlorodimethylsilane, chlorotriethylsilane, chlorotrimethylsilane, diethylisopropylsilyl chloride, dimethyl-n-octylchlorosilane, dimethylethylchlorosilane, dimethylisopropylchlorosilane, diphenylmethylchlorosilane, pentafluorophenyldimethylchlorosilane, tert-butyldimethylchlorosilane, tert-butyldiphenylchlorosilane, triisopropylsilyl chloride, or triphenylchlorosilane.

The process for synthesizing a methide series polysiloxane compound represented by general formula (5) is not particularly limited in the present invention. It is possible to mention a reaction in which compounds providing respective condensation units of the condensation unit (a), the condensation unit (b), and according to need the structural unit (c) are hydrolyzed, followed by condensation. For example, under coexistence of water, a publicly-known polymerization process, such as bulk polymerization, solution polymerization, suspension polymerization or emulsion polymerization, etc., may be conducted by an operation of any of batch-wise, half-continuous or continuous. Since bis(perfluoroalkanesulfonyl)methide moiety is strongly acid, compounds providing respective condensation units are hydrolyzed under coexistence of water, and a condensation reaction proceeds easily. In the condensation reaction, it is optional to add an acid such as sulfuric acid, a base such as ammonia, or a condensation reaction catalyst such as tin catalyst or titanium catalyst, as a reaction accelerating agent. In the present invention, a reaction container used for the polymerization reaction is not particularly limited.

[Silicone Resin]

It is possible to obtain a silicone resin containing bis(perfluoroalkanesulfonyl)methide group of the present invention by mixing a polysiloxane compound (e.g., a polysiloxane compound represented by general formula (5)) containing the condensation unit (a) with a cross-linking agent to prepare a polysiloxane composition, followed by a cross-linking. Furthermore, it is also possible to prepare a polysiloxane composition by additionally using the following polysiloxane compound represented by general formula (8) to conduct a cross-linking reaction.

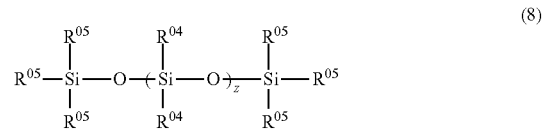

In the formula, each of $R^{04}$ and $R^{05}$ independently represents a hydrogen atom, alkyl group, alkenyl group, aryl group or hydroxy group, and at least two of $R^{04}$ and $R^{05}$ are cross-linking groups. It is preferable that two of them are cross-linking groups. The number z of the degree of polymerization represents an integer of 0-150.

In the polysiloxane compound represented by general formula (8), the substituent $R^{04}$ or $R^{05}$ other than the cross-linking group is preferably methyl group or phenyl group. It is preferably an organopolysiloxane in which z is 1-40. It is possible to use one type alone or a combination of at least two types. Exceeding 150 in degree of polymerization is not preferable, since it becomes difficult to be dissolved in solvent.

It is possible to obtain a polysiloxane compound represented by general formula (8) by subjecting a silane compound having a hydrolysable group, which is represented by general formula (10), to a hydrolysis-condensation reaction. On that occasion, the end can also be capped with the structural unit (c). Herein, $R^{04}$ and $R^{05}$ respectively correspond to $R^{02}$ and $R^{03}$ of general formula (10), and the explanations of $R^{02}$ and $R^{03}$ correspond to those. The reaction is conducted by the above-mentioned hydrolysis-condensation reaction of 2/z mol of a silane compound having one hydrolysable group relative to z mol of a silane compound having two hydrolysable groups. A cross-linking group may be contained in either silane compound. As such polysiloxane compound, it is optional to use one on the market, for example, CAT-104 (a cross-linking catalyst made by Shin-Etsu Chemical Co., Ltd., a product name).

A silicone resin having bis(perfluoroalkanesulfonyl)methide group of the present invention is obtained by a cross-linking reaction, but the manner of the cross-linking reaction is not limited.

As a cross-linking agent, it is possible to mention isocyanate compounds, epoxy compounds, aldehyde series compounds, chlorosilanes, alkoxysilanes, melamine series compounds, sulfur or sulfur compounds, or hydrosilanes, etc., which have a group that can react with a functional group (a cross-linking group), such as hydrogen atom, hydroxy group, mercapto group, carboxyl group, amino group, epoxy group, alkenyl group, alkynyl group, acryloyl group, methacryloyl group, chlorosilyl group, alkoxysilyl group or hydrosilyl group, etc., which is possessed by the methide series polysiloxane compound. Among these compounds, polyfunctional compounds having at least trifunctionality are preferable in terms of cross-linking density.

Furthermore, the cross-linking can also be conducted by a radical reaction using a peroxide or azo compound as a cross-linking agent. It can preferably be used in terms of durability, although one that is cross-linked by a radical reaction is not limited in reaction mechanism.

The isocyanate compound reacts with a hydroxy group, mercapto group, carboxyl group, amino group, etc. to form a cross-linking structure. For example, it is possible to mention diisocyanate compounds, such as 1,4-phenylenediisocyanate, 4,4'-diphenylmethanediisocyanate, 3,3'-dichlorobiphenyl-4,4'-diisocyanate, dicyclohexylmethane-4,4'-diisocyanate, hexamethylenediisocyanate, m-xylylenediisocyanate, tolylene-2,6-diisocyanate, trimethylhexamethylenediisocyanate, naphthalene diisocyanate, or isophoronediisocyanate, etc. Furthermore, it is possible to mention uretidinedione-type dimers, biuret-type trimers, or isocyanurate-type trimers of the diisocyanate compounds. Furthermore, it is possible to mention adducts of polyol, such as 1,3-propanediol or trimethylolpropane, of the diisocyanate. Furthermore, it is possible to mention triisocyanates, such as triphenylmethaneisocyanate and tris(isocyanatophanyl)thiophosphate, etc. Among these, hexamethylenediisocyanate is particularly preferable.

The epoxy compound reacts with a hydroxy group, mercapto group, carboxyl group, amino group, etc. to form a cross-linking structure. For example, it is possible to mention glycidyl ether series, glycidyl ester series, glycidyl amine series, or alicyclic series compounds, etc. Specifically, it is possible to mention 1,4-butanediol diglycidyl ether, 2,2-bis (4-glycidyloxyphenyl)propane, diglycidyl 1,2-cyclohexanedicarboxylate, 1,7-octadiene diepoxide, 1,5-hexadiene diepoxide, triglycidyl isocyanurate, neopentyl glycol diglycidyl ether, 1,3-butadiene monoepoxide, 1,2-epoxy-5-hexene, or 1,2-epoxy-9-decene, etc. Due to good reactivity, 1,4-butanediol diglycidyl ether is particularly preferable.

The aldehyde series compound reacts with a phenolic hydroxy group or the like to form a cross-linking structure. It is possible to mention formaldehyde, formalin aqueous solution, paraformaldehyde, trioxane, acetaldehyde, polyoxymethylene or propyonealdehyde, etc. Paraformaldehyde is particularly preferable, due to its good reactivity and easiness in handling.

The chlorosilanes react with hydroxy group, alkoxysilyl group, or the like, thereby becoming a siloxane bond and forming a cross-linking structure. For example, it is possible to mention dimethyldichlorosilane, diethyldichlorosilane, diphenyldichlorosilane, divinyldichlorosilane, methyldichlorosilane, ethyldichlorosilane, phenyldichlorosilane, vinyldichlorosilane, dichlorosilane, methyltrichlorosilane, ethyltrichlorosilane, phenyltrichlorosilane, vinyltrichlorosilane, trichlorosilane, tetrachlorosilane, 1,2-bis(trichlorosilyl)ethane, bis(trichlorosilyl)acetylene, 3-chloropropyltrichlorosilane, cyclohexyltrichlorosilane, trichloro(1H,1H,2H,2H-tridecafluoro-n-octyl)silane, trichloro-2-cyanoethylsilane, or phenyltrichlorosilane, etc. Dimethyldichlorosilane is particularly preferable, due to its good reactivity, low price and easy availability.

The alkoxysilanes condense with a halogen atom or alkoxy group to form a siloxane bond. For example, it is possible to mention dimethyldimethoxysilane, diethyldimethoxysilane, diphenyldimethoxysilane, divinyldimethoxysilane, methyldimethoxysilane, ethyldimethoxysilane, phenyldimethoxysilane, vinyldimethoxysilane, dimethoxysilane, methyltrimethoxysilane, ethyltrimethoxysilane, phenyltrimethoxysilane, vinyltrimethoxysilane, trimethoxysilane, tetramethoxysilane, dimethyldiethoxysilane, diethyldiethoxysilane, diphenyldiethoxysilane, divinyldiethoxysilane, methyldiethoxysilane, ethyldiethoxysilane, phenyldiethoxysilane, vinyldiethoxysilane, diethoxysilane, methyltriethoxysilane, ethyltriethoxysilane, phenyltriethoxysilane, vinyltriethoxysilane, triethoxysilane, tetraethoxysilane, 3-aminopropyltriethoxysilane, 3-(2-aminoethylamino)propyltrimethoxysilane, 3-(2-aminoethylamino)propyltriethoxysilane, bis[3-(trimethoxysilyl)propyl]amine, 1,2-bis(trimethoxysilyl)ethane, benzyltriethoxysilane, (3-bromopropyl)trimethoxysilane, 3-trimethoxysilylpropyl chloride, 2-cyanoethyltriethoxysilane, (chloromethyl)triethoxysilane, cyclohexyltrimethoxysilane, 2-(3,4-epoxycyclohexyl)ethyltrimethoxysilane, 3-glycidyloxypropyltrimethoxysilane, (3-mercaptopropyl)trimethoxysilane, (3-mercaptopropyl)triethoxysilane, 1,1,1-trifluoro-3-(trimethoxysilyl)propane, triethoxyphenylsilane, trimethoxyphenylsilane, trimethoxy(4-methoxyphenyl)silane, trimethoxy(p-tolyl)silane, etc. Dimethyldimethoxysilane is particularly preferable, due to its good reactivity, low price, and easy availability.

The melamine series compounds react with hydroxyl group, etc. to form a cross-linking structure. For example, it is possible to mention melamine, methylol melamine, or methylol melamine derivatives. It is possible to use a partially or completely etherified compound prepared by reacting a lower alcohol with methylol melamine. Furthermore, either a monomer or a polymer of at least dimer will do, and a mixture of these will do. Methylol melamine and its derivatives are particularly preferable, due to their good reactivity and easy handling.

The hydrosilane compound reacts with an alkenyl group, alkynyl group, acryloyl group, methacryloyl group, etc. to form a cross-linking structure. One having three SiH groups and a $C_{1-3}$ alkyl group or phenyl group in one molecule is preferable. It is represented by the following formula (9).

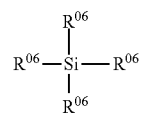

(9)

(In the formula, each of $R^{06}$ independently represents a hydrogen atom, a $C_{1-6}$ straight-chain or branched-chain alkyl group, a $C_{2-7}$ alkenyl group, or a $C_{6-8}$ aryl group, and at least three of $R^{06}$ are cross-linking groups or groups having a cross-linking group.) Specifically, methylsilane, ethylsilane, propylsilane, phenylsilane, etc. are preferable. In particular, phenylsilane is preferable.

The sulfur or sulfur compound reacts with an alkenyl group, alkynyl group, acryloyl group, methacryloyl group, etc. to form a cross-linking structure. As the sulfur or sulfur compound, it is possible to mention sulfur, tetramethylthiuram disulfide, tetraethylthiuram disulfide, tetrabutylthiuram disulfide, tetrakis(2-ethylhexyl)thiuram disulfide, dipentamethylenethiuram tetrasulfide, morpholine disulfide, or 2-(4'-morpholinodithio)benzothiazole, etc. Sulfur is particularly preferable, due to its low price and easy handling.

The peroxide forms a cross-linking structure by a radical reaction with an alkyl group, alkenyl group, alkynyl group, acryloyl group, methacryloyl group, etc. It is possible to mention benzoyl peroxide, dichlorobenzoyl peroxide, dicumyl peroxide, di-tert-butyl peroxide, 2,5-dimethyl-2,5-di(peroxide benzoate)hexyne-3,1,4-bis(tert-butylperoxyisopropyl)benzene, lauroyl peroxide, tert-butyl peracetate, 2,5-dimethyl-2,5-di(tert-butylperoxy)hexyne-3,2,5-trimethyl-2,5-di(tert-butylperoxy)hexane, ter-butylperbenzoate, tert-butyl perphenylacetate, tert-butyl perisobutyrate, tert-butyl per-sec-octoate, tert-butyl perpiparate, cumyl perpiparate, or tert-butyl perdiethylacetate, etc. Benzoyl peroxide or 2,5-dimethyl-2,5-di(tert-butylperoxy)hexyne-3 is particularly preferable, due to its good reactivity and superiority in mechanical characteristics of a film formed from the obtained silicone resin.

Furthermore, the azo compound forms a cross-linking structure by a radical reaction with an alkyl group, alkenyl group, alkynyl group, acryloyl group, methacryloyl group, etc. For example, it is possible to mention azobisisobutyronitrile or dimethylazoisobutyrate, etc. Azobisisobutyronitrile is particularly preferable, due to its low price and easy handling.

These cross-linking agents can also be used by selecting singularity or plurality. Furthermore, it is also possible to adjust the curing rate or pot life of the silicone resin, or properties of the silicone resin obtained, to a solid electrolyte membrane for fuel cells by making the type or usage of the cross-linking agent appropriate.

In the silicone resin production using these cross-linking agents, it is preferable to conduct an addition reaction, in which the cross-linking group is an alkenyl group, particularly an alkenyl group having a vinyl group at an end, and as the cross-linking agent a silane compound represented by general formula (9), particularly a monosubstituted silane where an alkyl group or phenyl group has been substituted, is used. In this addition reaction, contraction upon curing (cross-linking) is small, and therefore it is superior in dimensional stability. Thus, it is particularly preferable in the case of forming a membrane, such as a solid electrolyte membrane for fuel cells.

In the synthesis of a silicone resin of the present invention, the total amount of the polysiloxane compound represented by general formula (8) and the silane compound represented by general formula (9), which are reacted with the methide series polysiloxane compound represented by general formula (5), is 0.5 parts by mass to 3000 parts by mass, preferably 1 part by mass to 2000 parts by mass, relative to 100 parts by mass of the polysiloxane compound represented by general formula (5). If the above mixing amount is less than 0.5 parts by mass, it is not possible to obtain a cured material. It is not necessary to mix them to exceed 3000 parts by mass.

Mass of the silane compound represented by general formula (9) relative to the polysiloxane compound represented by general formula (8) is preferably 0% or more and less than 30% in terms of mass percentage. If it is used to exceed 30%, the obtained silicone resin becomes defective in curing. Therefore, it is not preferable.

As an addition reaction catalyst, it is possible to use any reaction catalyst, as long as it accelerates a hydrosilylation addition reaction of an alkenyl group in the methide series polysiloxane compound represented by general formula (5) with SiH group in the polysiloxane compound represented by general formula (8) or the silane compound represented by general formula (9). For example, it is possible to mention platinum group metals or compounds of these, such as platinum, palladium, rhodium, etc., chloroplatinic acid, alcohol-modified chloroplatinic acid, coordination compounds between chloroplatinic acid and olefins, vinyl siloxane or acetylenic compounds, tetrakis(triphenylphosphine)palladium, platinum divinylsiloxane, platinum cyclic vinylmethylsiloxane, tris(dibenzylidene acetone)diplatinum, bis(ethylene)tetrachlorodiplatinum, cyclooctadiene dichloroplatinum, bis(cyclooctadiene)platinum, bis(dimethylphenylphosphine)dichloroplatinum, platinum carbon, chlorotris(triphenylphosphine)rhodium, etc. In view of easy availability and catalytic activity, it is preferable to use particularly the above-mentioned platinum compounds as the reaction catalyst in the process for producing a silicone resin of the present invention.

The mixing amount of the reaction catalyst in the addition reaction is 0.5 ppm to 1,000 ppm, particularly a proportion of 1 ppm to 500 ppm being preferable, more preferably 10 ppm to 100 ppm, in terms of mass of the metal element in the reaction catalyst, relative to the total mass of the polysiloxane compound represented by general formula (5) and the polysiloxane compound represented by general formula (8), and/or the silane compound represented by general formula (9). If the mixing amount is less than 0.5 ppm, the addition reaction becomes extremely slow, or curing may not occur. If the mixing amount is too much, the cured resin membrane turns to have a black color.

In order to cure the silicone resin of the present invention, it is heated at 100° C. to 200° C. Preferably, it is set at 150° C. to 180° C. Although the heating time depends on the heating temperature, it is 1 to 48 hours, preferably 3 hours to 24 hours, more preferably 6 hours to 18 hours. In order to make the addition (curing) reaction proceed rapidly, solvent is used by 10 parts by weight to 500 parts by weight, more preferably 30 parts by weight to 300 parts by weight, relative to 100 parts by weight of the methide series polysiloxane compound represented by general formula (5). If it is less than 10 parts by mass, it is not dissolved sufficiently, thereby causing curing inferiority. The use exceeding 500 parts by mass is not necessary.

Furthermore, in a polymerization reaction by the hydrosilylation, it is possible to use various solvents that are generally used in this reaction. An organic solvent used is not particularly limited, as long as it does not interfere with the addition reaction and as long as it can dissolve raw material compounds used for a solid electrolyte membrane for fuel cells of the present invention. It is possible to mention ester series solvents such as ethyl acetate and butyl acetate, ether series solvents such as diethyl ether, diisopropyl ether and tetrahydrofuran, toluene, benzene, or hexane.

[Silicone Resin Composition]

According to need, a silicone resin of the present invention can be mixed with a reinforcing silica. That is, in order to provide a composition of the present invention with high tear property, it is possible to obtain a silicone resin that satisfies tear strength as a solid electrolyte membrane for fuel cells, by using, as a reinforcing agent, tiny powder silica, for example, fumed silica, precipitated silica, etc., in which specific surface area measured by BET method, which is a well-known specific surface area measurement method, is 50 $m^2/g$ or more.

Besides, as an inorganic filler, crystalline silica, hollow filler, silsesquioxane, fumed titanium dioxide, magnesium oxide, zinc oxide, iron oxide, aluminum hydroxide, magnesium carbonate, calcium carbonate, zinc carbonate, sheet mica, carbon black, diatomaceous earth, and glass fiber, or organoalkoxysilane compound, which is an organic silicon compound, etc. are used. Furthermore, silicone rubber powder or silicone resin powder is also usable. It is possible to obtain a proton conductivity of about 1 mS/cm to 100 mS/cm by using a silicone resin containing about 5 mass % to 90 mass % of a condensation unit having bis(perfluoroalkylsulfonyl)methide group of the present invention as a solid electrolyte membrane for fuel cells.

A solid electrolyte membrane for fuel cells, which is obtained by the present invention, has a good proton conductivity under a low water content condition. Furthermore, it is a solid electrolyte membrane for fuel cells, which has a heat resistance of about 260° C. and is chemically stable.

EXAMPLES

The present invention is specifically explained by the following examples. The examples shown by the following monomer synthesis examples, membrane preparation examples, and synthesis examples of the polysiloxane compounds show one example of embodiments and do not limit the present invention.

Monomer Synthesis Example 1

A three-necked flask equipped with a reflux condenser and having a volume of 100 ml was charged under nitrogen atmosphere with each of 100.2 g (0.313 mol) of 1,1-bis(trifluoromethanesulfonyl)-3-butene (hereinafter abbreviated as BTSB), 69.8 g of toluene, 11.7 mg (0.0001 parts by mass relative to BTSB) of dichloro(1,5-cyclooctadiene)platinum (II) (made by Tokyo Chemical Industry Co., Ltd.), and 155.0 g (155 parts by mass relative to BTSB) of triethoxysilane (made by Tokyo Chemical Industry Co., Ltd.). After that, under nitrogen atmosphere, it was stirred and mixed for three minutes. Then, the reaction was conducted for 11 hours, while this flask was heated by immersion in an oil bath adjusted to 85° C. After the termination of the reaction, triethoxysilane and toluene were distilled off and recovered under reduced pressure. Then, a distillation under reduced pressure was conducted to carry out a heating at 100° C. to 108° C. and distill it out under a reduced pressure of 533 Pa (4 mmHg), thereby obtaining 98.8 g of 4,4-bis(trifluoromethanesulfonyl)butyltriethoxysilane (hereinafter abbreviated as BTSB-TES).

The reaction formula is as follows. An addition reaction of triethoxysilane to BTSB by using dichloro(1,5-cyclooctadiene)platinum (II) as catalyst was conducted, thereby obtaining BTSB-TES, that is, 1a.

[Properties of BTSB-TES]
$^1$H NMR (solvent: chloroform-d); σ=4.85 (t, J=5.6 Hz, 1H), 3.83 (q, J=6.8 Hz, 6H), 2.52 (m, 2H), 1.86 (m, 2H), 1.23 (t, J=7.2 Hz, 9H), 0.70 (t, J=8.0 Hz, 2H) ppm
$^{19}$F NMR (solvent: chloroform-d); σ=−73.25 ppm

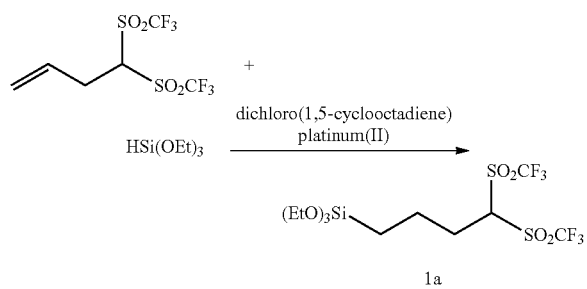

1a

Monomer Synthesis Example 2

A 100 ml, three-necked flask equipped with a reflux condenser was charged under nitrogen atmosphere with each of 6.4 g (0.020 mol) of BTSB, 23.8 g of toluene, 2.7 mg (0.0004 parts by mass relative to BTSB) of dichloro(1,5-cyclooctadiene)platinum (II) (made by Tokyo Chemical Industry Co., Ltd.), and 13.2 g (2.1 parts by mass relative to BTSB) of diethoxymethylsilane (made by Tokyo Chemical Industry Co., Ltd.). After that, under nitrogen atmosphere, it was stirred and mixed for three minutes. Then, the reaction was conducted for 16 hours, while this flask was heated by immersion in an oil bath adjusted to 90° C. After the termination of the addition reaction, diethoxymethylsilane and toluene were distilled off and recovered under reduced pressure. Then, a distillation under reduced pressure was conducted to carry out a heating at 85° C. to 90° C. and distill it out under a reduced pressure of 533 Pa (4 mmHg), thereby obtaining 4.8 g of 4,4-bis(trifluoromethanesulfonyl)butyldiethoxymethylsilane (hereinafter abbreviated as BTSB-DEMS).

The reaction formula is as follows. An addition reaction of diethoxysilane to BTSB by using dichloro(1,5-cyclooctadiene)platinum (II) as catalyst was conducted, thereby obtaining BTSB-DEMS, that is, 1b.

[Properties of BTSB-DEMS]
$^1$H NMR (solvent: chloroform-d); σ=4.90 (t, J=5.6 Hz, 1H), 3.84 (q, J=6.8 Hz, 4H), 2.50 (m, 2H), 1.86 (m, 2H), 1.24 (t, J=7.2 Hz, 6H), 0.60 (t, J=8.0 Hz, 2H), 0 (s, 3H) ppm
$^{19}$F NMR (solvent: chloroform-d); σ=−73.09 ppm

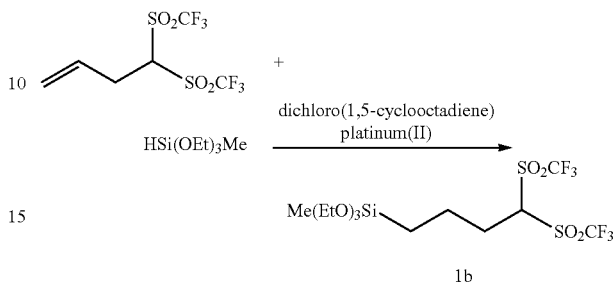

1b

Monomer Synthesis Example 3

A three-necked flask equipped with a reflux condenser and having a volume of 100 ml was charged under nitrogen atmosphere with each of 5.0 g (0.016 mol) of BTSB, 2.0 g of toluene, 0.8 mg (0.0002 parts by mass relative to BTSB) of dichloro(1,5-cyclooctadiene)platinum (II) (made by Tokyo Chemical Industry Co., Ltd.), and 2.1 g (0.43 parts by mass relative to BTSB) of dichloroethylsilane (made by Tokyo Chemical Industry Co., Ltd.). After that, under nitrogen atmosphere, it was stirred and mixed for three minutes. Then, the addition reaction was conducted for 1 hour, while this flask was heated by immersion in an oil bath adjusted to 50° C. After the termination of the addition reaction, toluene was distilled off and recovered under reduced pressure. Then, a distillation under reduced pressure was conducted to carry out a heating at 98° C. to 112° C. and distill it out under a reduced pressure of 533 Pa (4 mmHg), thereby obtaining 6.4 g of 4,4-bis(trifluoromethanesulfonyl)butyldichloroethylsilane (hereinafter abbreviated as BTSB-DCES).

The reaction formula is as follows. An addition reaction of dichloroethylsilane to BTSB by using dichloro(1,5-cyclooctadiene)platinum (II) as catalyst was conducted, thereby obtaining BTSB-DCES, that is, 1c.

[Properties of BTSB-DCES]
$^1$H NMR (solvent: tetrahydrofuran-d); σ=5.47 (t, J=5.6 Hz, 1H), 1.78 (m, 2H), 1.14 (m, 2H), 0.50 (t, J=8.8 Hz, 2H), 0.34 (m, 3H), 0.30 (m, 2H) ppm $^{19}$F NMR (solvent: tetrahydrofuran-d); σ=−73.19 ppm

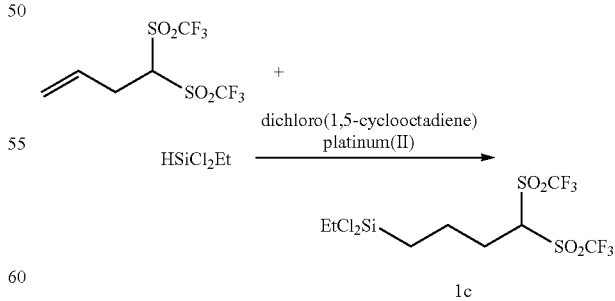

1c

Monomer Synthesis Example 4

A 100 ml, three-necked flask equipped with a reflux condenser was charged under nitrogen atmosphere with each of 11.6 g (0.036 mol) of BTSB, 11.6 g of toluene, 1.9 mg (0.0002 parts by mass relative to BTSB) of dichloro(1,5-cyclooctadiene)platinum (II) (made by Tokyo Chemical Industry Co., Ltd.), and 5.2 g (0.45 parts by mass relative to BTSB) of trichlorosilane (made by Tokyo Chemical Industry Co., Ltd.). After that, under nitrogen atmosphere, it was stirred and mixed for three minutes. Then, the addition reaction was conducted for 16 hours, while this flask was heated by immersion in an oil bath of 90° C. After the termination of the addition reaction, toluene was distilled off and recovered under reduced pressure. Then, a distillation under reduced pressure was conducted to carry out a heating at 100° C. to 115° C. and distill it out under a reduced pressure of 533 Pa (4 mmHg), thereby obtaining 14.5 g of 4,4-bis(trifluoromethanesulfonyl)butyltrichlorosilane (hereinafter abbreviated as BTSB-TCS).

The reaction formula is as follows. An addition reaction of trichlorosilane to BTSB by using dichloro(1,5-cyclooctadiene)platinum (II) as catalyst was conducted, thereby obtaining BTSB-TCS, that is, 1d.

[Properties of BTSB-TCS]
$^{1}$H NMR (solvent: tetrahydrofuran-d); σ=5.48 (t, J=5.6 Hz, 1H), 1.82 (dt, J=9.0, 6.0 Hz, 2H), 1.21 (m, 2H), 0.91 (t, J=9.0 Hz, 2H) ppm
$^{19}$F NMR (solvent: tetrahydrofuran-d); σ=−73.15 ppm

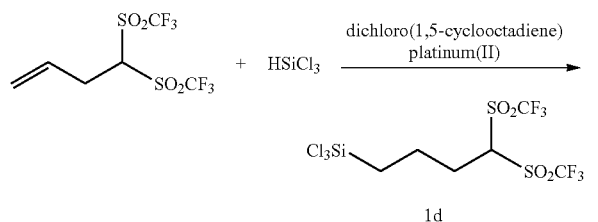

1d

Monomer Synthesis Example 5

A three-necked flask equipped with a reflux condenser and having a volume of 100 ml was charged under nitrogen atmosphere with each of 126.7 g (0.393 mol) of BTSB, 68.7 g of toluene, 15.2 mg (0.0002 parts by mass relative to BTSB) of dichloro(1,5-cyclooctadiene)platinum (II) (made by Tokyo Chemical Industry Co., Ltd.), and 50.0 g (0.4 parts by mass relative to BTSB) of dichloromethylsilane (made by Tokyo Chemical Industry Co., Ltd.). After that, under nitrogen atmosphere, it was stirred and mixed for three minutes. Then, the addition reaction was conducted for 30 minutes, while this flask was heated by immersion in an oil bath adjusted to 50° C. After the termination of the addition reaction, toluene was distilled off and recovered under reduced pressure. Then, a distillation under reduced pressure was conducted to carry out a heating at 105° C. to 115° C. and distill it out under a reduced pressure of 533 Pa (4 mmHg), thereby obtaining 163.0 g of 4,4-bis(trifluoromethanesulfonyl)butyldichloromethylsilane (hereinafter abbreviated as BTSB-DCMS).

The reaction formula is as follows. An addition reaction of dichloromethylsilane to BTSB by using dichloro(1,5-cyclooctadiene)platinum (II) as catalyst was conducted, thereby obtaining BTSB-DCMS, that is, 1e.

[Properties of BTSB-DCMS]
$^{1}$H NMR (solvent: tetrahydrofuran-d); σ=5.47 (t, J=5.4 Hz, 1H), 1.77 (dt, J=9.0, 6.3 Hz, 2H), 1.15 (m, 2H), 0.51 (t, J=8.8 Hz, 2H), 0 (s, 3H) ppm
$^{19}$F NMR (solvent; tetrahydrofuran-d); σ=−73.21 ppm

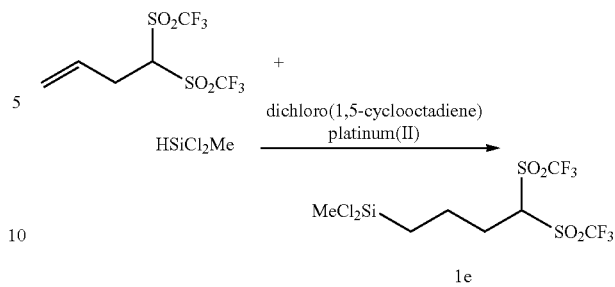

1e

Monomer Synthesis Example 6

A 100 ml, three-necked flask equipped with a reflux condenser was charged under nitrogen atmosphere with each of 48.6 g (0.152 mol) of BTSB, 16.0 g of toluene, 11.4 mg (0.0002 parts by mass relative to BTSB) of dichloro(1,5-cyclooctadiene)platinum (II) (made by Tokyo Chemical Industry Co., Ltd.), and 15.2 g (0.31 parts by mass relative to BTSB) of chlorodimethylsilane (made by Tokyo Chemical Industry Co., Ltd.). After that, under nitrogen atmosphere, it was stirred and mixed for three minutes. Then, the addition reaction was conducted for 30 minutes, while this flask was heated by immersion in an oil bath adjusted to 50° C. After the termination of the addition reaction, toluene was distilled off and recovered under reduced pressure. Then, a distillation under reduced pressure was conducted to carry out a heating at 101° C. to 111° C. and distill it out under a reduced pressure of 533 Pa (4 mmHg), thereby obtaining 56.1 g of 4,4-bis (trifluoromethanesulfonyl)butylchlorodimethylsilane (hereinafter abbreviated as BTSB-CDMS).

The reaction formula is as follows. An addition reaction of chlorodimethylsilane to BTSB by using dichloro(1,5-cyclooctadiene)platinum (II) as catalyst was conducted, thereby obtaining BTSB-CDMS, that is, 1f.

[Properties of BTSB-CDMS]
$^{1}$H NMR (solvent: chloroform-d); σ=5.47 (t, J=5.6 Hz, 1H), 2.07 (m, 2H), 1.45 (m, 2H), 0.50 (t, J=8.5 Hz, 2H), 0 (m, 6H) ppm
$^{19}$F NMR (solvent: chloroform-d); σ=−73.51 ppm

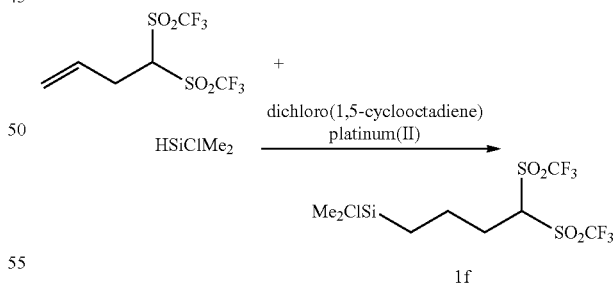

1f

Polysiloxane Compound Synthesis Example 1

A polysiloxane compound of the invention was synthesized by using BTSB-DCMS (Compound 1e) obtained by the above [Monomer synthesis example 5].

A glass flask was charged with 28.1 g of BTSB-DCMS and 5.9 g of dimethylvinylchlorosilane. After adding 10.8 g of tetrahydrofuran, the flask was cooled by immersion in an iced bath. Then, 5.0 g of ion-exchanged water was gradually added dropwise to the flask by spending 10 minutes. After stirring and mixing for 1 hour at room temperature (20° C.), it was diluted with isopropyl ether, followed by washing the organic layer three times with water and distilling the solvent away with an evaporator. While the obtained viscous liquid was heated at 150° C., it was dried in a vacuum, thereby obtaining 23.3 g of a pale-yellow liquid (Polysiloxane compound 2e) (vinyl group content=1.32 mmol/g=1.32 millimoles/gram). In the following, the reaction formula is shown.

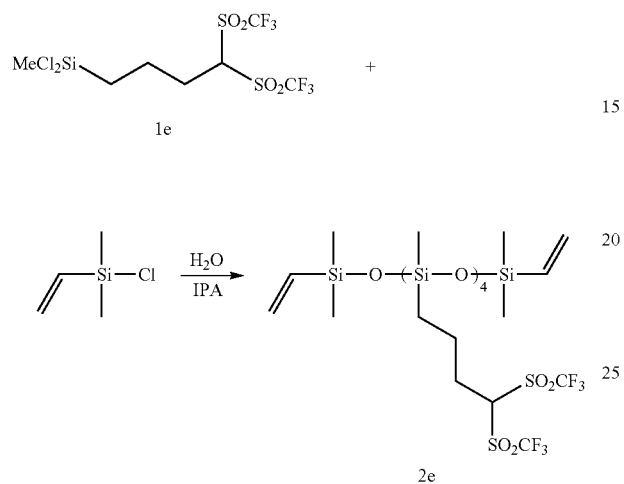

2e

Polysiloxane Compound Synthesis Example 2

A polysiloxane compound of the present invention was synthesized by using BTSB-TCS (Compound 1d) obtained by the above [Monomer synthesis example 4].

A glass flask was charged with 6.6 g of BTSB-TCS and 0.6 g of dimethylvinylchlorosilane. After adding 5.3 g of isopropyl alcohol, the flask was cooled by immersion in an iced bath. Then, 1.0 g of ion-exchanged water was gradually added dropwise to the flask by spending 10 minutes. After stirring and mixing for 1 hour at room temperature (20° C.), it was diluted with isopropyl ether, followed by washing the organic layer three times with water and distilling the solvent away with an evaporator. While the obtained viscous liquid was heated at 150° C., it was dried in a vacuum, thereby obtaining 4.1 g of a pale-yellow liquid (Polysiloxane compound 2d) (vinyl group content=1.97 mmol/g). In the following, the reaction formula is shown.

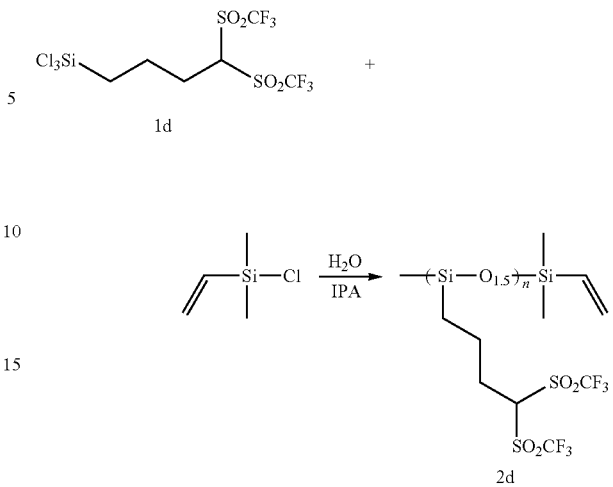

2d n is the degree of polymerization, and n=3-5 is a major component.

Membrane Preparation Example 1

A solid electrolyte membrane for fuel cells was prepared by using a pale-yellow liquid (Polysiloxane compound 2e: vinyl group content=1.32 mmol/g) obtained by the above [Polysiloxane compound synthesis example 1].

In a glass flask, to 100 parts (it refers to parts by mass, and it is the same in the following.) of Compound 2e, that is, bis(trifluoromethanesulfonyl)butyl(methyl)siloxane (vinyl group content=0.0012 mol %), which is capped with dimethylvinylsilyl groups at both ends of the molecular chain, 18 parts of 1,1,3,3-tetramethyldisiloxane, 4 parts of phenylsilane, 71 parts of butyl acetate, and 0.1 parts (50 ppm) of dichloro(1,5-cyclooctadiene)platinum (II) were added, followed by mixing. After the mixing, it was put into a thermostat. After heating in a stepwise fashion at 80° C. for 30 minutes, 100° C. for 30 minutes, 120° C. for 30 minutes, and 150° C. for 30 minutes, it was applied on a polytetrafluoroethylene (hereinafter abbreviated as PTFE) plate by a bar coater to have a uniform film thickness. Then, heating was conducted at 180° C. for 15 hours to obtain a cured membrane (A). In the following, the reaction formula is shown by using a schematic drawing.

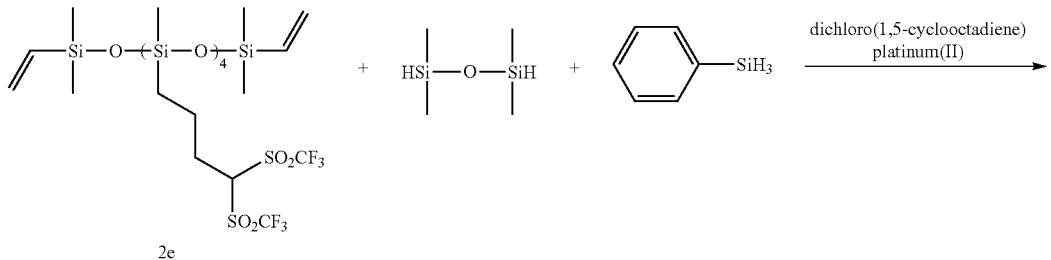

-continued

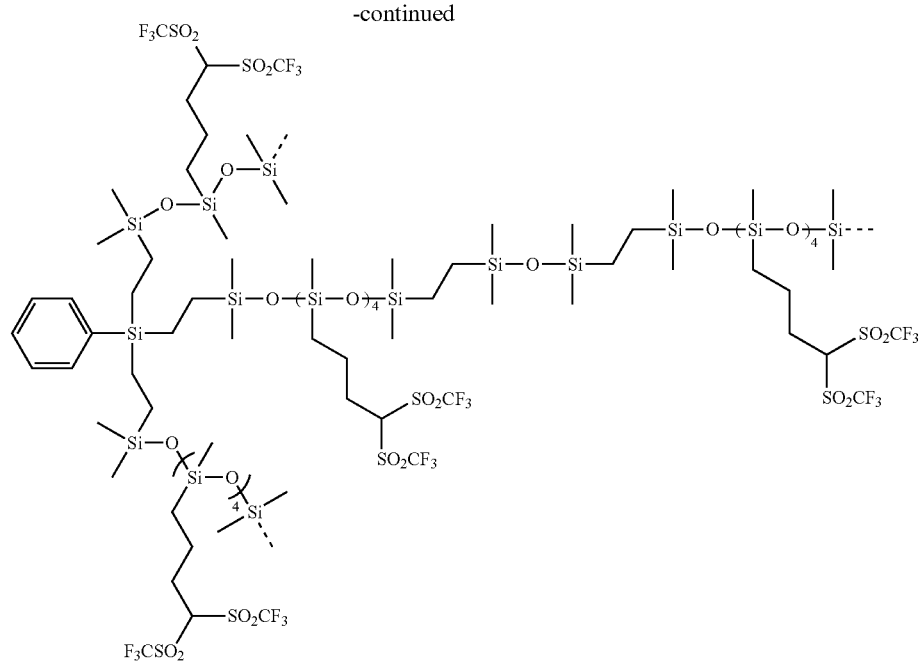

As a result of the TG-DTA measurement of the obtained cured membrane (A), the pyrolysis start temperature was 260° C.

Furthermore, a publicly-known Fenton's test was conducted for examining radical resistance. Chemical stability of the cured membrane (A) was tested. There was conducted three times in total an operation, in which the cured membrane (A) was immersed in a test liquid prepared by adding 2 ppm $Fe^{2+}$ to a 3 mass % hydrogen peroxide solution maintained at 90° C. in a glass flask, and it was taken out in two hours. As the test liquid when starting each immersion, a newly prepared one was used.

The cured membrane (A) after the termination of the immersion test was washed with 1N hydrochloric acid aqueous solution and ion-exchanged water, followed by drying under reduced pressure at 80° C. using a vacuum oven. The cured membrane (A) after the drying under reduced pressure did not have a shape change, and its percentage of mass change was not greater than 2%.

Thus, it was confirmed to have heat resistance, due to pyrolysis temperature of the cured membrane (A) being 260° C., and to be superior in chemical stability due to radical resistance as a result of Fenton's test.

Membrane Preparation Example 2

A solid electrolyte membrane for fuel cells was prepared by using a pale-yellow liquid (Polysiloxane compound 2e: vinyl group content=0.0012 mol %) obtained by the above [Polysiloxane compound synthesis example 1].

In a glass flask, to 100 parts of Polysiloxane Compound 2e, that is, bis(trifluoromethanesulfonyl)butyl(methyl)siloxane (vinyl group content=1.32 mmol/g), which contains dimethylvinylsilyl groups and is capped with dimethylvinylsilyl groups at both ends of the molecular chain, 29 parts of 1,3-divinyltetramethyldisiloxane, 57 parts of 1,1,3,3-tetramethylsiloxane, 10 parts of phenylsilane, 32 parts of butyl acetate, and 0.1 parts (50 ppm) of dichloro(1,5-cyclooctadiene)platinum (II) were added, followed by mixing. After the mixing, it was put into a thermostat. After heating in a stepwise fashion at 80° C. for 30 minutes, 100° C. for 30 minutes, 120° C. for 30 minutes, and 150° C. for 30 minutes, it was uniformly applied on a PTFE plate by a bar coater. Then, heating was conducted at 180° C. for 15 hours to obtain a cured membrane (B). In the following, the reaction formula is shown.

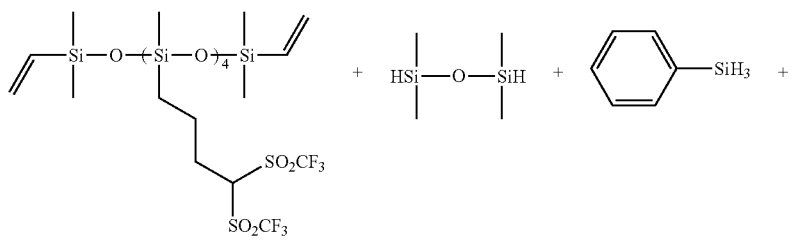

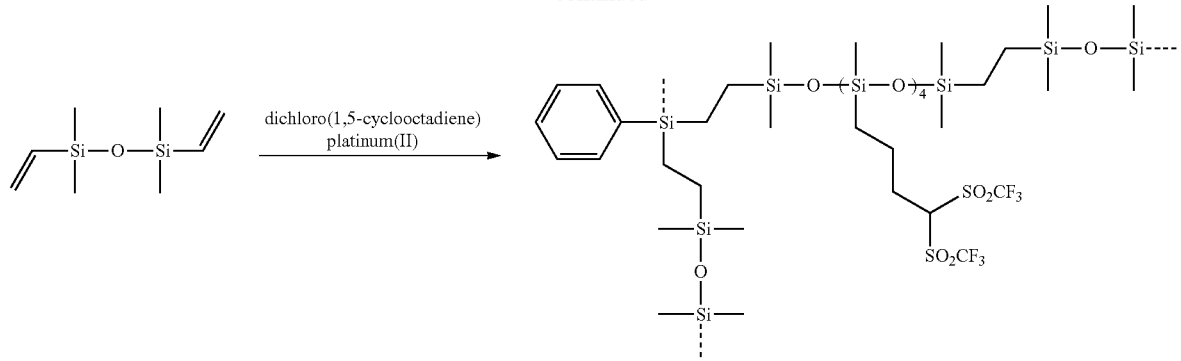

As a result of the TG-DTA measurement of the obtained cured membrane (B), the pyrolysis start temperature was 260° C.

Similar to the preparation example 1 of the solid electrolyte membrane for fuel cells, Fenton's test was conducted. As a result, the cured membrane (B) after the drying under reduced pressure did not have a shape change, and its percentage of mass change was not greater than 2 mass %.

Thus, it was confirmed to have heat resistance, due to pyrolysis temperature of the cured membrane (B) being 260° C., and to be superior in chemical stability due to radical resistance as a result of Fenton's test.

Membrane Preparation Example 3

A solid electrolyte membrane for fuel cells was prepared by using a pale-yellow liquid (Polysiloxane Compound 2e: vinyl group content=1.32 mmol/g) obtained by the above [Polysiloxane compound synthesis example 1].

In a glass flask, to 100 parts of Polysiloxane Compound 2e, that is, bis(trifluoromethanesulfonyl)butyl(methyl)siloxane (vinyl group content=0.0012 mol %), which is capped with dimethylvinylsilyl groups at both ends of the molecular chain, 120 parts of 1,3-divinyltetramethyldisiloxane, 190 parts of 1,1,3,3-tetramethylsiloxane, 37 parts of phenylsilane, 62 parts of butyl acetate, and 0.1 parts (50 ppm) of dichloro (1,5-cyclooctadiene)platinum (II) were added, followed by mixing. After the mixing, it was put into a thermostat. After heating in a stepwise fashion at 80° C. for 30 minutes, 100° C. for 30 minutes, 120° C. for 30 minutes, and 150° C. for 30 minutes, it was uniformly applied on a PTFE plate by a bar coater. Then, heating was conducted at 180° C. for 15 hours to obtain a cured membrane (C).

As a result of the TG-DTA measurement of the obtained cured membrane (C), the pyrolysis start temperature was 260° C.

Similar to the membrane preparation example 1, Fenton's test was conducted. As a result, the cured membrane (C) after the drying under reduced pressure did not have a shape change, and its percentage of mass change was not greater than 2 mass %.

Thus, it was confirmed to have heat resistance, due to pyrolysis temperature of the cured membrane (C) being 260° C., and to be superior in chemical stability due to radical resistance as a result of Fenton's test.

Membrane Preparation Example 4

A solid electrolyte membrane for fuel cells was prepared by using a pale-yellow liquid (Polysiloxane Compound 2d: vinyl group content=0.0006 mol %) obtained by the above [Polysiloxane compound synthesis example 2].

In a glass flask, to 100 parts of Compound 2d, that is, dimethylvinylsilyl group-containing bis(trifluoromethane-sulfonyl)butylsiloxane resin (vinyl group content=1.97 mmol/g), 34 parts of a dimethylsiloxane-condensed polysiloxane compound (made by Shin-Etsu Chemical Co., Ltd., product number: CAT-104), 200 parts of butyl acetate, and 0.1 parts (50 ppm) of dichloro(1,5-cyclooctadiene)platinum (II) were added, followed by mixing. After the mixing, it was put into a heating furnace. After heating in a stepwise fashion at 80° C. for 30 minutes, 100° C. for 30 minutes, 120° C. for 30 minutes, and 150° C. for 30 minutes, it was applied on a PTFE plate by a bar coater to have a uniform thickness. Then, heating was conducted at 180° C. for 15 hours to obtain a cured membrane (D). In the following, the reaction formula is shown.

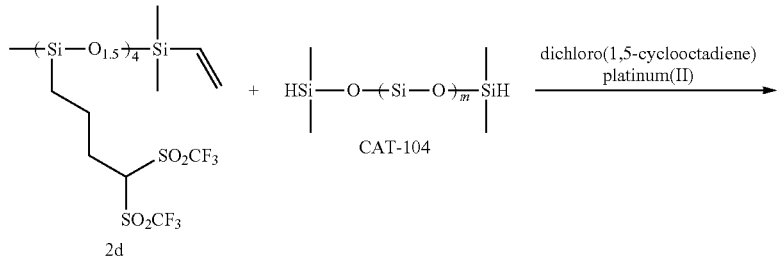

-continued

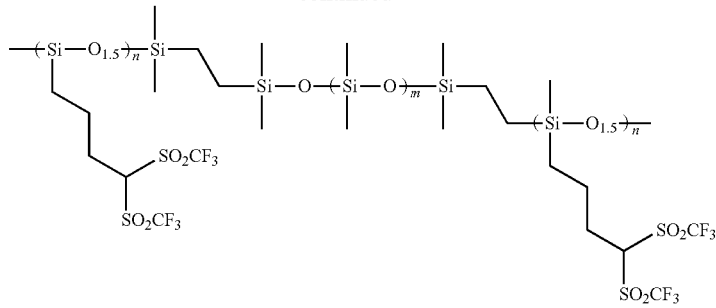

m and n represent the degrees of polymerization, each of m=16-20 and n=3-5 is a major component.

As a result of the TG-DTA measurement of the obtained cured membrane (D), the pyrolysis start temperature was 260° C.

Similar to the membrane preparation example 1, Fenton's test was conducted. As a result, the cured membrane (D) after the drying under reduced pressure did not have a shape change, and its percentage of mass change was not greater than 2 mass %.

Thus, it was confirmed to have heat resistance, due to pyrolysis temperature of the cured membrane (D) being 260° C., and to be superior in chemical stability due to radical resistance as a result of Fenton's test.

Comparative Example 1

A solid electrolyte membrane for fuel cells, sold by US Aldrich Co., made of a perfluorocarbonsulfonic acid series polymer, and having a product name of Nafion and a product number of 112, was dried under a heated condition at 180° C. for 15 hours.

[Proton Conductivity]

Proton conductivities of the solid electrolyte membranes for fuel cells of the present invention, prepared in Examples (Membrane preparation examples 1-4), and the solid electrolyte membrane (trade name, Nafion) for fuel cells of Comparative Example 1 were measured, and the results are shown in Table 1.

Proton conductivity was measured by the following method. The solid electrolyte membrane for fuel cells was cut into 50 mm×10 mm, and platinum electrodes disposed to have a distance of 5 mm and the membrane were tightly attached with each other. An electrochemical impedance measurement apparatus (made by Gamry Instruments Co., model number: VFP600) was connected to the electrodes, and an alternating-current impedance measurement was conducted in a frequency region of 1 Hz to 1 MHz to determine alternating-current resistance. Specific resistance of the proton conductive membrane was calculated by the following formula from a gradient between the distance between the electrodes and the resistance. Alternating-current impedance was calculated from inverse number of specific resistance. Moisture content was calculated by measuring the weight of water in the membrane after the proton conductivity measurement.

TABLE 1

|  | Membrane | Bismethide Introduction Amount-Theoretical calculation value-(mmol/g) | Proton Conductivity (S/cm) | Moisture Content* (%) |
| --- | --- | --- | --- | --- |
| Examples | Membrane Prep. Ex. 1 | 1.93 | $1.6 \times 10^{-2}$ | 9.1 |
|  | Membrane Prep. Ex. 2 | 1.22 | $7.3 \times 10^{-3}$ | 3.6 |
|  | Membrane Prep. Ex. 3 | 1.31 | $6.6 \times 10^{-3}$ | 3.2 |
|  | Membrane Prep. Ex. 4 | 0.80 | $5.2 \times 10^{-3}$ | 2.3 |
| Comparative Example | Com. Ex. 1 | Ion exchange capacity 0.90 | $5.0 \times 10^{-3}$ | 4.7 |

Specific resistance R (Ω · cm) = 1 (cm) × membrane thickness (cm) × resistance/line gradient (Ω/cm)
Moisture content* (%) = 100 × {(weight of water in the membrane)/(weight of membrane after proton conductivity measurement)}
Weight of water in the membrane = (weight of membrane after proton conductivity measurement) − (weight of membrane after vacuum drying)

In Table 1, as compared with the solid electrolyte membrane (trade name, Nafion) for fuel cells of Comparative Example 1, the solid electrolyte membranes for fuel cells of Examples (Membrane Preparation Examples 1-4) were confirmed to have good proton conductivities even under low-humidified conditions having low moisture contents.

[Methanol Permeation Rate]

Methanol permeation rate was measured by the following method. The solid electrolyte membrane for fuel cells immersed in ion-exchanged water for one day was put between separable-type glass cells made by Techno-sigma Co. One cell was charged with 20 ml of 10 wt % methanol aqueous solution, and the other cell was charged with 20 ml of ion-exchanged water. At 25° C., under stirring, methanol concentration of the ion-exchanged water was measured by a gas chromatograph (made by Shimadzu Corporation, model number: GC2010).

The measurement results of methanol permeation rates of the membranes obtained by Examples (Membrane Preparation Examples 1-4) and Comparative Example 1 are shown in Table 2.

TABLE 2

|  | Membrane | Methanol permeation rate ($10^{-6}$ mol/cm$^2$ · min) |
| --- | --- | --- |
| Examples | Membrane Prep. Ex. 1 | 0.4 |
|  | Membrane Prep. Ex. 2 | 0.2 |
|  | Membrane Prep. Ex. 3 | 0.2 |
|  | Membrane Prep. Ex. 4 | 0.1 |
| Comparative Example | Comparative Example 1 | 33.4 |

As is clear from Table 2, the membranes obtained by Examples (Membrane Preparation Examples 1-4) of the present invention showed low values by about three digits or more in methanol permeability. The membranes of the present invention were confirmed to be superior as solid electrolyte membranes for fuel cells in suppressing methanol permeation.

The invention claimed is:

1. A polysiloxane compound comprising the following condensation unit (a),

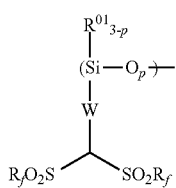

wherein each of $R^{01}$ is independently a hydrogen atom, alkyl group, alkenyl group or aryl group and represents an organic group optionally having a cross-linking group, W represents a single bond or bivalent group, and $R_f$ represents a $C_{1-9}$ perfluoroalkyl group, and p represents 1, 2 or 3.

2. A polysiloxane compound according to claim 1, wherein W is a single bond, a $C_{1-10}$ straight-chain or branched-chain alkylene group, or a bivalent organic group represented by general formula (6),

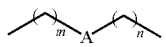

wherein m represents an integer of 2-5, n represents an integer of 0-5, and A represents any group represented by the following formula (7)

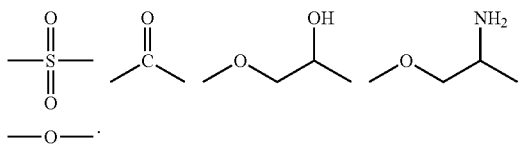

3. A polysiloxane compound according to claim 1, further comprising the following condensation unit (b),

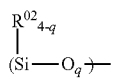

wherein each of $R^{02}$ is independently a hydrogen atom, alkyl group, alkenyl group or aryl group and represents an organic group optionally having a cross-linking group, and p represents 1, 2, 3 or 4.

4. A polysiloxane compound according to claim 1, wherein an end of the polysiloxane skeleton is capped with a group represented by the following formula (c),

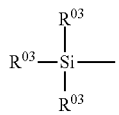

wherein each of $R^{03}$ independently represents a hydrogen atom, alkyl group, alkenyl group or aryl group and represents an organic group optionally having a cross-linking group.

5. A polysiloxane compound according to claim 3, comprising 2-150 units of the condensation unit (a) and 0-150 units of the condensation unit (b).

6. A polysiloxane compound according to claim 1, which comprises as the cross-linking group at least one selected from the group consisting of hydroxy group, mercapto group, carboxyl group, amino group, epoxy group, alkenyl group, alkynyl group, acryloyl group, methacryloyl group, chlorosilyl group, alkoxysilyl group, and hydrosilyl group.

7. A polysiloxane composition comprising a cross-linking agent and the polysiloxane compound according to claim 1.

8. A polysiloxane composition according to claim 7, further comprising a siloxane compound represented by the following formula (8),

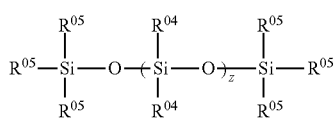

wherein each of $R^{04}$ and $R^{05}$ independently represents a hydrogen atom, alkyl group, alkenyl group or aryl group, and at least two of $R^{04}$ and $R^{05}$ have cross-linking groups, and z represents an integer of 0-150.

9. A polysiloxane composition according to claim 7, wherein the cross-linking agent is at least one selected from the group consisting of isocyanate compounds, epoxy compounds, aldehyde series compounds, chlorosilanes, alkoxysilanes, melamine series compounds, sulfur or sulfur compounds, hydrosilanes, peroxides, and azo compounds.

10. A polysiloxane composition according to claim 7, wherein the cross-linking agent is a silane compound represented by the following formula (9),

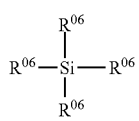

wherein each of $R^{06}$ independently represents a hydrogen atom, a $C_{1-6}$ straight-chain or branched-chain alkyl group, a $C_{2-7}$ alkenyl group, or a $C_{6-8}$ aryl group, and at least three of $R^{06}$ are cross-linking groups or groups having a cross-linking group.

11. A silicone resin obtained by subjecting the polysiloxane composition according to claim 7 to a cross-linking reaction.

12. A solid electrolyte membrane comprising the silicone resin according to claim 11.

13. A solid electrolyte membrane according to claim 12, wherein content of the condensation unit (a) component is 5 mass % or more of mass of the membrane.

14. A methide series silane compound represented by general formula (4),

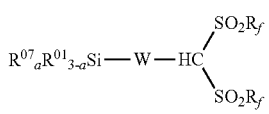
(4)

wherein $R^{07}$ represents a fluorine atom, chlorine atom, bromine atom, iodine atom or alkoxy group, $R^{01}$ represents a hydrogen atom, alkyl group, alkenyl group or aryl group, $R_f$ represents a $C_{1-9}$ perfluoroalkyl group, and a represents an integer of 0-3, and W represents a single bond or bivalent organic group.

15. A methide series silane compound according to claim 14, wherein W is a single bond, a $C_{1-10}$ straight-chain or branched-chain alkylene group, or a bivalent organic group represented by general formula (6)

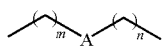
(6)

wherein m represents an integer of 2-5, n represents an integer of 0-5, and A represents any group represented by the following formula (7)

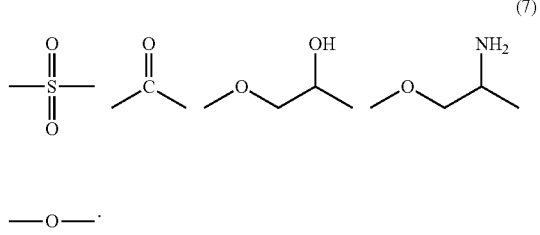
(7)

16. A methide series silane compound according to claim 14, wherein each of $R^{01}$ and $R^{07}$ is independently a $C_{1-6}$ alkoxy group, a $C_{1-6}$ straight-chain or branched-chain alkyl group, a $C_{2-6}$ alkenyl group, or a $C_{6-8}$ aryl group.

17. A methide series silane compound according to claim 14, wherein a is an integer of 1-3.

* * * * *